US012807689B2

(12) United States Patent
Bergmann

(10) Patent No.: US 12,807,689 B2
(45) Date of Patent: Nov. 24, 2026

(54) ANTI-ADRENOMEDULLIN (ADM) BINDER FOR USE IN THERAPY OR PREVENTION OF SYMPTOMS OF ILLNESS

(71) Applicant: AdrenoMed AG, Hennigsdorf (DE)

(72) Inventor: Andreas Bergmann, Berlin (DE)

(73) Assignee: ADRENOMED AG, Hennigsdorf (DE)

( * ) Notice: Subject to any disclaimer, the term of this patent is extended or adjusted under 35 U.S.C. 154(b) by 448 days.

(21) Appl. No.: 16/650,474

(22) PCT Filed: Sep. 25, 2018

(86) PCT No.: PCT/EP2018/075987

§ 371 (c)(1),
(2) Date: Mar. 25, 2020

(87) PCT Pub. No.: WO2019/057992

PCT Pub. Date: Mar. 28, 2019

(65) Prior Publication Data

US 2022/0227854 A1 Jul. 21, 2022

(30) Foreign Application Priority Data

Sep. 25, 2017 (EP) .................................... 17192999
Nov. 23, 2017 (EP) .................................... 17203370

(51) Int. Cl.
*C07K 16/22* (2006.01)
*A61K 9/00* (2006.01)
*A61K 39/00* (2006.01)

(52) U.S. Cl.
CPC ............ *C07K 16/22* (2013.01); *A61K 9/0019* (2013.01); *A61K 39/00* (2013.01); *C07K 2317/56* (2013.01); *C07K 2317/565* (2013.01); *C07K 2317/76* (2013.01); *C07K 2317/92* (2013.01); *C07K 2318/20* (2013.01)

(58) Field of Classification Search
None
See application file for complete search history.

(56) References Cited

U.S. PATENT DOCUMENTS

| | | | | |
|---|---|---|---|---|
| 8,961,967 | B2 * | 2/2015 | Strohl | A61P 11/06 530/387.2 |
| 9,304,127 | B2 * | 4/2016 | Bergmann | A61K 39/3955 |
| 12,338,281 | B2 * | 6/2025 | Bergmann | C07K 16/26 |
| 2017/0218056 | A1 | 8/2017 | Naparstek et al. | |
| 2020/0249246 | A1 | 8/2020 | Bergmann | |

FOREIGN PATENT DOCUMENTS

| | | | |
|---|---|---|---|
| CN | 104144948 | A | 11/2014 |
| EP | 2594587 | A1 | 5/2013 |
| EP | 2594588 | A1 | 5/2013 |
| JP | 2015502930 | A | 1/2015 |
| JP | 2016521351 | A | 7/2016 |
| RU | 2596925 | C2 | 9/2016 |
| WO | 20130072512 | A1 | 5/2013 |
| WO | WO 2017/186928 | * | 11/2017 |
| WO | 2018109228 | A1 | 6/2018 |
| WO | 2019057992 | A2 | 3/2019 |

OTHER PUBLICATIONS

Blet et al., Intensive Care Medicine Experimental, 2015, 3 (Suppl 1):A618.*
Geven et al., Critical Care, 22:159, published online Jun. 13, 2018.*
NCT02991508, Adrecizumab Phase 1 Trial, Mar. 15, 2017 version, pp. 1-15, downloaded from ClinicalTrials.gov on Dec. 5, 2023.*
Geven et al., Br J Clin Pharmacol, 84:2129-2141, available Jun. 1, 2018.*
Author Guidelines for British Journal of Clinical Pharmacology, 24 pages, https://bpspubs.onlinelibrary.wiley.com/hub/journal/136521251/author-guidlines.html, accessed Aug. 26, 2024.*
Geven et al., Intensive Care Med Exp 5 (Suppl 2):0427, published Sep. 20, 2017.*
Critical Care editorial policies, 52 pages, https://www.biomedcentral.com/getpublished/editorial-policies#availability+of+data+and+materials, accessed Aug. 26, 2024.*
Adrenomed Press Release dated Jun. 14, 2018, 4 pages.*
Geven C, et al. Effects of the Humanized Anti-Adrenomedullin Antibody Adrecizumab (HAM8101) on Vascular Barrier Function and Survival in Rodent Models of Systemic Inflammation and Sepsis. Shock. Dec. 2018;50(6):648-654. doi: 10.1097/SHK.0000000000001102.*
Geven, Christopher; Bergmann, Andreas; Kox, Matthijs; Pickkers, Peter. Vascular Effects of Adrenomedullin and the Anti-Adrenomedullin Antibody Adrecizumab in Sepsis. SHOCK 50(2):p. 132-140, Aug. 2018. DOI: 10.1097/SHK.0000000000001103.*
NCT03085758, Treatment of Patients with Early Septic Shock and Bio-Adrenomedullin (ADM) Concentration > 70 pg/ml with ADRECIZUMAB (AdrenOSS-2), Dec. 19, 2017 version, pp. 1-25, downloaded from ClinicalTrials.gov on Sep. 9, 2024.*
Intensive Care Medicine Experimental editorial policies, 26 pages, https://icm-experimental.springeropen.com/submission-guidelines/preparing-your-manuscript/research-articles, accessed Sep. 9, 2024.*
Caironi et al., Chest, 152(2):312-320, Aug. 2017.*

(Continued)

*Primary Examiner* — Marianne P Allen
(74) *Attorney, Agent, or Firm* — Millen, White, Zelano & Branigan P.C.; Ryan R. Pool

(57) ABSTRACT

Subject matter of the present invention is an anti-adrenomedullin (ADM) antibody or an anti-adrenomedullin antibody fragment or anti-ADM non-Ig scaffold for use in therapy or prevention of symptoms of illness and/or for use in therapy or prevention of diseases characterized by said symptoms. The symptoms of illness may be selected from the group of nausea, headache, muscle aches, back pain, shivering, vomiting in a subject wherein said antibody or fragment or scaffold may bind to ADM of amino acids 1 to 52 (SEQ ID NO: 1), or to fragments thereof.

4 Claims, 7 Drawing Sheets

Specification includes a Sequence Listing.

(56) References Cited

OTHER PUBLICATIONS

International Search Report dated Mar. 21, 2019 issued in corresponding PCT/EP2018/075987 application (7 pages).
J. Struck et al., "Epitope Specificity of Anti-Adrenomedullin Antibodies Determines Efficacy of Morality Reduction in a Cecal Ligation and Puncture Mouse Model", Intensive Care Medicine Experimental, vol. 1, No. 1 (2013) pp. 1-11.
Anonymous: "Adrecizumab-LPS Study—Full Text View—ClinicalTrials.gov" XP055460516—Retrieved from Internet: URL:https://clinicaltrials.gov/ct2/show/NCT03083171 (Mar. 19, 2018) pp. 1-8.
Ka Peterson et al., "Effect of Adrenomedullin on the Cerebral Circulation: Relevance to Primary Headache Disorders", Cephalalgia, vol. 29, No. 1 (2009) pp. 23-30.
A. F. Russo et al., "CGRP as a Neuropeptide in Migraine: Lessons From Mice", British Journal of Clinical Pharmacology, vol. 80, No. 3 (2015) pp. 403-414.
C. Geven et al., "Adrenomedullin and Adrenomedullin-Targeted Therapy as Treatment Strategies Relevant for Sepsis", Frontiers in Immunology, vol. 9 (2018) pp. 1-14.
Albert Michelle A. et al: "Plasma Concentration of C-Reactive Protein and the Calculated Framingham Coronary Heart Disease Risk Score", Circulation, Jul. 15, 2003, vol. 108, No. 2, pp. 161-165.
Anonymous, "Migraine", The Lancet, Mar. 25, 2021, p. 1. URL: https://www.thelancet.com/series-do/migraine (Retrieved Mar. 29, 2022).
Aron Adrian et al: "Inflammatory biomarkers are unrelated to endothelial-mediated vasodilation in physically active young men", Journal of Human Sport & Exercise, 2012, vol. 7, Iss. 2, pp. 581-588.
Ashina Messoud et al: Migraine: epidemiology and systems of care, The Lancet, Mar. 25, 2021, vol. 397, No. 10283, pp. 1-11.
Badri H. et al: "Optimization of Radiation Dosing Schedules for Proneural Glioblastoma", Journal of Mathematical Biology, Jun. 21, 2015, vol. 72, pp. 1301-1336.
Chen Ching et al: "Generation and Analysis of Random Point Mutations in an Antibody CDR2 Sequence: Many Mutated Antibodies Lose Their Ability to Bind Antigen", Journal of Experimental Medicine, The Rockefeller University Press, Sep. 1, 1992, vol. 176, Iss. 3, pp. 855-866.
Dillingh Marlous R. et al.: "Characterization of inflammation and immune cell modulation induced by low-dose LPS administration to healthy volunteers", Journal of Inflammation, 2014, vol. 11, No. 28, pp. 1-9.
Hamzaoui Olfa et al.: "How Do I Integrate Hemodynamic Variables When Managing Septic Shock?", Korean Journal of Critical Care Medicine, Nov. 2016, vol. 31, No. 4, pp. 265-275.
Incorvaia Cristoforo et al: "Omalizumab, an anti-immunoglobulin E antibody: state of the art", Drug Design, Development and Therapy, Feb. 7, 2014, vol. 2014, No. 8, pp. 197-207.
Kitamura, 2013, vol. 45, No. 12, pp. 1496-1502.
Kushner Irving et al: "What Does Minor Elevation of C-Reactive Protein Signify?", The American Journal of Medicine, Feb. 2006, vol. 119, No. 2, pp. 166.e17-166.e28.
Lobo Suzana M. A. et al: "C-Reactive Protein Levels Correlate With Mortality and Organ Failure in Critically Ill Patients", Chest, vol. 123, Issue 6, Jun. 2003, pp. 2043-2049.
Marino Rossella et al.: "Plasma adrenomedullin is associated with short-term mortality and vasopressor requirement in patients admitted with sepsis", Critical Care, Feb. 17, 2014, vol. 18, No. R34, pp. 1-7.
Papaioannou Theodore G et al: "Mean arterial pressure values calculated using seven different methods and their associations with target organ deterioration in a single-center study of 1878 individuals", Hypertension Research, 2016, vol. 39, pp. 640-647.
Pradhan Saurabh et al: "The role of C-reactive protein as a diagnostic predictor of sepsis in a multidisciplinary Intensive Care Unit of a tertiary care center in Nepal", Indian Journal of Critical Care Medicine, Jul. 2016, vol. 20, Iss. 7, pp. 417-420.
Ravi V. et al: "Correlation of tumor necrosis factor levels in the serum and cerebrospinal fluid with clinical outcome in Japanese encephalitis patients", Journal of Medical Virology, Dec. 7, 1998, vol. 51, Iss. 2, pp. 132-136.
Simon Tim-Philipp et al: "Plasma adrenomedullin in critically ill patientswith sepsis after major surgery: A pilot study", Journal of Critical Care, Abstract, Apr. 2017, vol. 38, pp. 1-6.
Su Chinh Tran-To et al: "The role of Antibody $V_K$ Framework 3 region towards Antigen binding: Effects on recombinant production and Protein L binding", Scientific Reports, Jun. 19, 2017, vol. 7, No. 3766, pp. 1-7.
Thiele C. et al: "P107 Effects of a non-neutralizing humanized monoclonal anti-adrenomedullin antibody in a porcine two-hit model of hemorrhage and septic shock", 38th International Symposium on Intensive Care and Emergency Medicine, Brussels, Belgium, Mar. 20-23, 2018, Critical Care, vol. 22(Suppl 1), No. 82, pp. 1, 42.
Weber Julia et al: "Sandwich Immunoassay for Bioactive Plasma Adrenomedullin", The Journal of Applied Laboratory Medicine, vol. 2, Issue 2, Sep. 1, 2017, pp. 222-233.

* cited by examiner

Distribution of illness score by treatment arm at T270 and T300

A)

B)

A)

B)

C)

D)

E)

ANTI-ADRENOMEDULLIN (ADM) BINDER FOR USE IN THERAPY OR PREVENTION OF SYMPTOMS OF ILLNESS

SEQUENCE LISTING

The instant application contains a Sequence Listing which has been submitted electronically in ASCII format and is hereby incorporated by reference in its entirety. Said ASCII copy, created on May 28, 2021, is named BOEHMERP-0282_SL.txt and is 25,730 bytes in size.

Subject matter of the present invention is an anti-adrenomedullin (ADM) antibody or an anti-adrenomedullin antibody fragment or anti-ADM non-Ig scaffold for use in therapy or prevention of symptoms of illness and/or for use in therapy or prevention of diseases characterized by said symptoms. The symptoms of illness may be selected from the group of nausea, headache, muscle aches, back pain, shivering, vomiting in a subject wherein said antibody or fragment or scaffold may bind to ADM of amino acids 1 to 52 (SEQ ID NO: 1), or to fragments thereof.

BACKGROUND

Diverse diseases or illnesses may have common, partially non-specific symptoms that can range from unpleasant to unbearable for the individual suffering from therefrom. Quite often individuals experiencing more than one symptom need to take several drugs to experience alleviation of these symptoms. There is an ongoing need for new forms of therapy or prevention of symptoms associated with many different underlying diseases or illnesses. In particular, it would be helpful to provide medicaments or drugs that can be used in the therapy or prevention of more than one symptom associated with an underlying disease or illness. The present invention addresses this need.

The peptide adrenomedullin (ADM) was described for the first time in 1993 (Kitamura K et al. 1993. *Biochemical and Biophysical Research Communications Vol.* 192 (2): 553-560) as a novel hypotensive peptide comprising 52 amino acids, which had been isolated from a human pheochromocytome. In the same year, cDNA coding for a precursor peptide comprising 185 amino acids and the complete amino acid sequence of this precursor peptide were also described. The precursor peptide, which comprises, inter alia, a signal sequence of 21 amino acids at the N-terminus, is referred to as "preproadrenomedullin" (pre-proADM). In the present description, all amino acid positions specified usually relate to the pre-proADM which comprises the 185 amino acids. The peptide adrenomedullin (ADM) is a peptide which comprises 52 amino acids (SEQ ID NO: 1) and which comprises the amino acids 95 to 146 of pre-proADM, from which it is formed by proteolytic cleavage. To date, only a few fragments of the peptide fragments formed in the cleavage of the pre-proADM have been more exactly characterized, in particular the physiologically active peptides adrenomedullin (ADM) and "PAMP", a peptide comprising 20 amino acids (22-41) which follows the 21 amino acids of the signal peptide in pre-proADM. The discovery and characterization of ADM in 1993 triggered intensive research activity, the results of which have been summarized in various review articles, in the context of the present description, reference being made in particular to the articles to be found in an issue of "Peptides" devoted to ADM in particular (Editorial, Takahashi K 2001. *Peptides* 22:1691) and (Eto T 2001. *Peptides* 22: 1693-1711). A further review is (Hinson et al. 2000. *Endocrine Reviews* 21(2):138-167). In the scientific investigations to date, it has been found, inter alia, that ADM may be regarded as a poly-functional regulatory peptide. It is released into the circulation in an inactive form extended by glycine (Kitamura K et al. 1998. *Biochem. Biophys. Res. Commun.* 244(2):551-555). There is also a binding protein (Pio R. et al. 2001. *The Journal of Biological Chemistry* 276(15):12292-12300) which is specific for ADM and probably likewise modulates the effect of ADM. Those physiological effects of ADM as well as of PAMP which are of primary importance in the investigations to date were the effects influencing blood pressure.

ADM is an effective vasodilator, and it is possible to associate the hypotensive effect with the particular peptide segments in the C-terminal part of ADM. It has furthermore been found that the above-mentioned further physiologically active peptide PAMP formed from pre-proADM likewise exhibits a hypotensive effect, even if it appears to have an action mechanism differing from that of ADM.

It has furthermore been found that the concentrations of ADM, which can be measured in the circulation and other biological liquids are, in a number of pathological states, significantly above the concentrations to be found in healthy control persons. Thus, the ADM level in patients with congestive heart failure, myocardial infarction, kidney diseases, hypertensive disorders, diabetes mellitus, in the acute phase of shock and in sepsis and septic shock are significantly increased, although to different extents. The PAMP concentrations are also increased in some of said pathological states, but the plasma levels are lower relative to ADM ((Eto, T., supra). It is furthermore known that unusually high concentrations of ADM are to be observed in sepsis, and the highest concentrations in septic shock (cf. (Eto, T., "supra) and (Hirata et al. *Journal of Clinical Endocrinology and Metabolism* 1996. 81(4): 1449-1453; Ehlenz K et al. 1997. *Exp Clin Endocrinol Diabetes* 105: 156-162); Tomoda Y. et al. 2001. *Peptides* 22: 1783-1794; Ueda S. et al. 1999. *Am. J. Respir. Crit. Care Med.* 160: 132-136; and Wang P. *Peptides* 2001, 22: 1835-1840).

There is only limited knowledge about the role of adrenomedullin in migraine. As adrenomedullin has vasodilatory effects within the cerebral circulation, it is hypothesized to be involved in migraine. On the one hand, the administration of human ADM intravenous infusion to patients suffering from migraine did not induce significantly more headache or migraine compared with placebo (Petersen et al. 2008. *Cephalalgia* 29: 23-30). Moreover, Akcali et al. reported low plasma adrenomedullin levels in the natural course of migraine patients (Akcali A. 2016. *Medical Science and Discovery* 3(4): 153-158). On the other hand, it has been stated by Kis et al. that there is a need for the development of novel, potent, specific and possibly non-peptide receptor antagonists as potential therapeutic tools for the suppression of ADM-mediated proliferative effects as anti-migraine drugs (Kis et al. 2003. *Hypertens Res* 26 (*Suppl*): S61-S70).

Definitions

Before describing the invention in detail, it is deemed expedient to provide definitions for certain technical terms used throughout the description. Although the present invention will be described with respect to particular embodiments, this description is not to be construed in a limiting sense. Before describing in detail exemplary embodiments of the present invention, definitions important for understanding the present invention are given.

As used in this specification and in the appended claims, the singular forms of "a" and "an" also include the respective plurals unless the context clearly dictates otherwise.

In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%.

It is to be understood that the term "comprising" is not limiting. For the purposes of the present invention the term "consisting" of is considered to be a preferred embodiment of the term "comprising" of. If hereinafter a group is defined to comprise at least a certain number of embodiments, this is meant to also encompass a group, which preferably consists of these embodiments only.

It is also to be understood that the terminology used herein is for the purpose of describing particular embodiments only, and is not intended to limit the scope of the present invention that will be limited only by the appended claims.

As used herein, the term "nausea" refers to a sensation of unease and discomfort in the upper stomach with an involuntary urge to vomit (Metz A. 2017. *Australian Family Physician Vol.* 36 (9): 688-692). It may precede vomiting, but a person can have nausea without vomiting. When prolonged, it is a debilitating symptom. Nausea is a non-specific symptom, which means that it has many possible causes. Some common causes of nausea are motion sickness, dizziness, migraine, fainting, low blood sugar, gastroenteritis (stomach infection) or food poisoning. Nausea is a side effect of many medications including chemotherapy, or morning sickness in early pregnancy. Nausea may also be caused by anxiety, disgust and depression.

As used herein, the term "headache" is the symptom of pain anywhere in the region of the head or neck. It occurs in migraines (sharp or throbbing pains), tension-type headaches, and cluster headaches (Waldman et al. 2014. *J Yoga Phys Ther* 2014, 4:1). There is also an increased risk of depression in those with severe headaches. Headaches can occur as a result of many conditions whether serious or not. There are a number of different classification systems for headaches. It is well-recognized that causes of headaches may include fatigue, sleep deprivation, stress, effects of medications, the effects of recreational drugs, viral infections, loud noises, common colds, head injury, rapid ingestion of a very cold food or beverage, and dental or sinus issues.

Headaches are broadly classified as "primary" or "secondary" (Oleson 2005. *Functional Neurology* 20(2): 61-68). Primary headaches are benign, recurrent headaches not caused by underlying disease or structural problems. For example, migraine is a type of primary headache. While primary headaches may cause significant daily pain and disability, they are not dangerous. The four categories of primary headaches are: migraine, tension-type headache (TTH) cluster headache and other trigeminal autonomic cephalalgias, and other primary headaches.

Secondary headaches, which are of organic, metabolic or drug-induced origin, are caused by an underlying disease, like an infection, head injury, vascular disorders, brain bleed or tumors. Secondary headaches can be harmless or dangerous. A migraine is a primary headache disorder characterized by recurrent headaches that are moderate to severe (for review see: Diener et al. 2012. *Nat Rev Neurol.* 8(3):162-71). Typically, the headaches affect one half of the head, are pulsating in nature, and last from two to 72 hours. Associated symptoms may include nausea, vomiting, and sensitivity to light, sound, or smell. The pain is generally made worse by physical activity. Up to one-third of people have an aura: typically a short period of visual disturbance, which signals that the headache will soon occur. Occasionally, an aura can occur with little or no headache following it.

As used herein, the terms "muscle aches" or "muscle pain", also termed "myalgia", refer to a symptom of many diseases and disorders (for review see: Kyriakides et al. 2013. *European Journal of Neurology* 20: 997-1005). The most common causes are the overuse or over-stretching of a muscle or group of muscles. Myalgia without a traumatic history is often due to viral infections. Longer-term myalgias may be indicative of a metabolic myopathy, some nutritional deficiencies or chronic fatigue syndrome.

As used herein, the term "back pain" refers to painful sensations in the any part of the back. Episodes of back pain may be acute, sub-acute, or chronic depending on the duration. The pain may be characterized as a dull ache, shooting or piercing pain, or a burning sensation. The pain may radiate into the arms and hands as well as the legs or feet, and may include paresthesia (tingling with no apparent cause), weakness or numbness in the legs and arms. The anatomic classification of back pain follows the segments of the spine: neck pain (cervical), middle back pain (thoracic), lower back pain (lumbar) or coccydynia (tailbone or sacral pain) with the lumbar vertebrae area most common for pain. The pain may originate from the muscles, nerves, bones, joints or other structures in the vertebral column (spine), however, internal structures such as the gallbladder and pancreas may also cause referred pain in the back (Cohen et al. 2008. *BMJ.* 337:a2718).

As used herein, the term "shivering" (also called "shuddering") is a bodily function in response to early hypothermia or just feeling cold in warm-blooded animals. When the core body temperature drops, the shivering reflex is triggered to maintain homeostasis. Skeletal muscles begin to shake in small movements, creating warmth by expending energy. Shivering can also be a response to a fever, as a person may feel cold. During fever the hypothalamic set point for temperature is raised. The increased set point causes the body temperature to rise (pyrexia), but also makes the patient feel cold until the new set point is reached. Severe chills with violent shivering are called rigors. Rigors occur because the patient's body is shivering in a physiological attempt to increase body temperature to the new set point. Shivering can also appear after surgery, known as post-anesthetic shivering.

As used herein, the term "vomiting", also known as emesis and throwing up, among other terms, is the involuntary, forceful expulsion of the contents of one's stomach through the mouth and sometimes the nose (Metz A. 2017. *Australian Family Physician Vol.* 36 (9): 688-692). Vomiting can be caused by a wide variety of conditions; it may present as a specific response to ailments like gastritis or poisoning, or as a non-specific sequela of disorders ranging from brain tumors and elevated intracranial pressure to overexposure to ionizing radiation.

As used herein, the symptoms of illnesses or diseases in a patient in need of therapy and/or prevention of such symptoms are selected from the groups of disease indications comprising inflammatory conditions, autoimmune diseases, metabolic diseases, brain diseases, cardiovascular diseases and drug-induced diseases.

Below, the types of symptoms and illnesses associated herewith are provided in form of non-limiting lists. It is noted that the herein described therapy or prevention may be directed to more than one type of symptom. Further, it is noted that a given medical indication, illness, or disease may be associated with more than one of the symptoms.

The symptom "nausea" may be associated with illnesses inside the abdomen, e.g. obstructing disorders (for example pyloric obstruction, small bowel obstruction, colonic obstruction, superior mesenteric artery syndrome), enteric infections (for example viral or bacterial infection), inflammatory diseases (such as cholecystitis, pancreatitis, appendicitis, hepatitis), sensorimotor dysfunction (for example, gastroparesis, intestinal pseudo-obstruction, gastroesophageal reflux disease, chronic idiopathic nausea, functional vomiting, cyclic vomiting syndrome, rumination syndrome) or biliary colic; illnesses outside the abdomen, e.g. cardiopulmonary disorder (such as cardiomyopathy, myocardial infarction), inner-ear diseases (such as motion sickness, labyrinthitis, malignancies), intracerebral disorders (for example hemorrhage, abscess, hydrocephalus, malignancies), psychiatric illnesses (for example anorexia and bulimia nervosa, depression), post-operative vomiting, nausea associated with medications and drugs (for example chemotherapy and biologics therapy, antibiotics, anti-arrhythmics, digoxin, oral hypoglycemic medications, oral contraceptives), nausea associated with endocrine/metabolic diseases (such as pregnancy, uremia, ketoacidosis, thyroid and parathyroid disease, adrenal insufficiency), nausea due to intoxication because of liver failure, alcohol abuse, etc.

The symptom "back pain" may be associated with illnesses due to inflammation, especially in the acute phase, which typically lasts from two weeks to three months, and may be associated with lumbago, trauma, injury, infections, cancer (especially cancers known to spread to the spine like breast, lung and prostate cancer), etc.

The symptom "myalgia" or "muscle pain" may be associated with injury or trauma, including sprains, hematoma, or overuse, wherein a muscle was used too much, too often, including protecting a separate injury, chronic tension, muscle pain due to rhabdomyolysis, associated with, e.g., viral infections, compression injury, drug-related, e.g., due to fibrates and statins, ACE inhibitors, cocaine, some anti-retroviral drugs, severe potassium deficiency, fibromyalgia, Ehlers-Danlos syndrome, auto-immune disorders (including for example mixed connective tissue disease, Systemic lupus erythematosus, polymyalgia rheumatic, Myositis, such as polymyositis, dermatomyositis, and inclusion body myositis, multiple sclerosis, Myalgic Encephalomyelitis (chronic fatigue syndrome), Familial Mediterranean fever, Polyarteritis nodosa, Devic's disease, Morphea, Sarcoidosis), metabolic diseases (such as carnitine palmitoyltransferase II deficiency, Conn's syndrome, Adrenal insufficiency, Hyperthyroidism, Hypothyroidism, Diabetes, Hypogonadism, as well as Channelopathy, Stickler Syndrome, Hypokalemia, Hypotonia (Low Muscle Tone), Exercise intolerance, Mastocytosis, Peripheral neuropathy, Eosinophilia myalgia syndrome, Barcoo Fever, herpes, hemochromatosis also known as iron overload disorder, delayed onset muscle soreness, AIDS, HIV infections, tumor-induced osteomalacia, hypovitaminosis D, myocardial infarction.

The symptom "headache" may be associated with primary headaches. 90% of all headaches are primary headaches. Primary headaches usually first start when people are between 20 and 40 years old. The most common types of primary headaches are migraines and tension-type headaches. They have different characteristics. Migraines typically present with pulsing head pain, nausea, photophobia (sensitivity to light) and phonophobia (sensitivity to sound). Tension-type headaches usually present with non-pulsing "bandlike" pressure on both sides of the head, not accompanied by other symptoms. Other very rare types of primary headaches include: cluster headaches: short episodes (15-180 minutes) of severe pain, usually around one eye, with autonomic symptoms (tearing, red eye, nasal congestion) which occur at the same time every day. Cluster headaches can be treated with triptans and prevented with prednisone, ergotamine or lithium; trigeminal neuralgia or occipital neuralgia characterized by shooting face pain, hemicrania continua, i.e., continuous unilateral pain with episodes of severe pain; primary stabbing headaches, e.g., recurrent episodes of stabbing "ice pick pain" or "jabs and jolts" for 1 second to several minutes without autonomic symptoms (tearing, red eye, nasal congestion); Primary cough headache that starts suddenly and lasts for several minutes after coughing, sneezing or straining (anything that may increase pressure in the head). Serious causes (see secondary headaches red flag section) must be ruled out before a diagnosis of "benign" primary cough headache can be made; primary exertional headache characterized by throbbing, pulsatile pain which starts during or after exercising, lasting for 5 minutes to 24 hours. The mechanism behind these headaches is unclear, possibly due to straining causing veins in the head to dilate, causing pain; primary sex headache characterized by a dull, bilateral headache that starts during sexual activity and becomes much worse during orgasm; hypnic headache; secondary headaches that may be caused by problems elsewhere in the head or neck. Some of these are not harmful, such as cervicogenic headache (pain arising from the neck muscles), medication overuse headache in those using excessive painkillers for headaches, meningitis characterized by inflammation of the meninges which presents with fever and meningismus, or stiff neck; bleeding inside the brain (intracranial hemorrhage); subarachnoid hemorrhage (acute, severe headache, stiff neck without fever); ruptured aneurysm, arteriovenous malformation, intraparenchymal hemorrhage; temporal arteritis, i.e., an inflammatory disease of arteries common in the elderly (average age 70), polymyalgia rheumatic; acute closed angle glaucoma (increased pressure in the eyeball); post-ictal headaches that happen after a convulsion or other type of seizure, as part of the period after the seizure (the post-ictal state); gastrointestinal disorders may cause headaches, including *Helicobacter pylori* infection, celiac disease, non-celiac gluten sensitivity, irritable bowel syndrome, inflammatory bowel disease, gastroparesis, and hepatobiliary disorders. The treatment of the gastrointestinal disorders may lead to a remission or improvement of headaches.

The term headache is defined as primary or secondary headache. Primary headache is defined as migraine, tension-type headache (TTH), cluster headache and other trigeminal autonomic cephalalgias, and other primary headaches.

Diagnosis or assessment of headache is well-established in the art. Assessment may be performed based on subjective measures, such as patient characterization of symptoms. For example, migraine may be diagnosed based on the following criteria: 1) episodic attacks of headache lasting 4 to 72 hours; 2) with two of the following symptoms: unilateral pain, throbbing, aggravation on movement, and pain of moderate or severe intensity; and 3) one of the following symptoms: nausea or vomiting, and photophobia or phonophobia (Goadsby et al., *N. Engl. J. Med.* 346:257-270, 2002).

The symptom "shivering" may be associated with fever, cold sensitivity, menopause, panic attack, anxiety, bacterial infection, rickettsial infection, viral infection, drug withdrawal, etc.

The symptom "vomiting" may be associated with gastritis (inflammation of the gastric wall), gastroenteritis, gastroesophageal reflux disease, celiac disease, non-celiac gluten sensitivity, pyloric stenosis, bowel obstruction, overeating, acute abdomen and/or peritonitis, ileus, food allergies (often in conjunction with hives or swelling); cholecystitis, pancreatitis, appendicitis, hepatitis; food poisoning, allergic reaction to cow's milk proteins, e.g., milk allergy or lactose intolerance; motion sickness, Meniere's disease, concussion, cerebral hemorrhage, migraine, brain tumors, benign intracranial hypertension and hydrocephalus, metabolic disturbances such as hypercalcemia, Uremia adrenal insufficiency, hypoglycemia, hyperglycemia, drug reaction, alcohol intoxication, opioid uptake, selective serotonin reuptake inhibitors; use of chemotherapy drugs; gastric inflammation caused by a range of viruses and bacteria, e.g., norovirus, influenza; or psychiatric/behavioral illnesses such as bulimia nervosa and purge disorder.

DETAILED DESCRIPTION OF EMBODIMENTS OF THE INVENTION

Below, embodiments of the invention are provided. It is noted that generally embodiments can be combined with any other embodiment of the same category (product, process, use, method).

One embodiment of the invention relates to an anti-ADM antibody or an anti-ADM antibody fragment or anti-ADM non-Ig scaffold for use in therapy or prevention of symptoms of illness or for the use in therapy or prevention of illnesses characterized by such symptoms. The symptoms may be selected from the group of nausea, headache, muscle aches, back pain, shivering, vomiting in a subject in need thereof. Said antibody or fragment or scaffold binds to mature ADM, e.g., to ADM of amino acids 1 to 52 (SEQ ID NO: 1), or fragments of mature ADM, e.g., Mid-Regional ADM (MR-ADM) (SEQ ID NO: 3), or to N-terminal ADM (SEQ ID NO: 4), as detailed below.

Therefore, another embodiment of the invention relates to an anti-ADM antibody or an anti-ADM antibody fragment or anti-ADM non-Ig scaffold for use in therapy or prevention of symptoms of illness or for the use in therapy or prevention of illnesses characterized by such symptoms, wherein said antibody or fragment or scaffold binds to mature ADM, e.g., to ADM of amino acids 1 to 52 (SEQ ID NO: 1), or to fragments thereof as defined above.

A further embodiment of the invention relates to an anti-ADM antibody or an anti-ADM antibody fragment or anti-ADM non-Ig scaffold for use in therapy or prevention of illnesses characterized by symptoms such as nausea, headache, muscle aches, back pain, shivering, vomiting in a subject in need thereof, and wherein said antibody or fragment or scaffold binds to mature ADM, e.g., to ADM of amino acids 1 to 52 (SEQ ID NO: 1), or to fragments thereof as defined above.

In further embodiments, the invention relates to an anti-ADM antibody or an anti-ADM antibody fragment or anti-ADM non-Ig scaffold for use in therapy or prevention of illnesses in a subject in need thereof, wherein said antibody or fragment or scaffold binds to mature ADM, e.g., to ADM of amino acids 1 to 52 (SEQ ID NO: 1), or to fragments thereof as defined above, and wherein the illnesses are selected from indications, wherein the amount of C-reactive protein (CRP) in a sample is ≥10 mg/L, and/or wherein the amount of TNF in a sample is ≥50 pg/ml, and/or wherein the amount of bio-ADM in a sample is ≥43 pg/ml, and/or wherein the mean arterial pressure is decreased.

In a further embodiment, the invention relates to an anti-ADM antibody or an anti-ADM antibody fragment or anti-ADM non-Ig scaffold for use in therapy or prevention of illnesses in a subject in need thereof, wherein said antibody or fragment or scaffold binds to mature ADM, e.g., to ADM of amino acids 1 to 52 (SEQ ID NO: 1), or to fragments thereof as defined above, and wherein the illness is migraine.

In a further embodiment, the invention relates to an anti-ADM antibody or an anti-ADM antibody fragment or anti-ADM non-Ig scaffold for use in therapy or prevention of illnesses in a subject in need thereof, wherein said antibody or fragment or scaffold binds to mature ADM, e.g., to ADM of amino acids 1 to 52 (SEQ ID NO: 1), or to fragments thereof as defined above, and wherein the illness is migraine, wherein the subject in need thereof has an amount of C-reactive protein (CRP) in a sample of ≥10 mg/L, and/or wherein the amount of TNF in a sample is ≥50 pg/ml, and/or wherein the amount of bio-ADM in a sample is ≥43 pg/ml, and/or wherein the mean arterial pressure is decreased.

In a further embodiment, the invention relates to an anti-ADM antibody or an anti-ADM antibody fragment or anti-ADM non-Ig scaffold for use in therapy or prevention of illnesses in a subject in need thereof, wherein said antibody or fragment or scaffold binds to mature ADM, e.g., to ADM of amino acids 1 to 52 (SEQ ID NO: 1), or to fragments thereof as defined above, and wherein the illness is migraine, wherein the subject in need thereof has an amount of C-reactive protein (CRP) in a sample of ≥10 mg/L, and/or wherein the amount of TNF in a sample is ≥50 pg/ml, and/or wherein the amount of bio-ADM in a sample is ≥43 pg/ml, and/or wherein the mean arterial pressure is decreased, and wherein the subject in need thereof shows at least one of the following disease symptoms selected from the group of nausea, headache, muscle aches, back pain, shivering, vomiting.

In one embodiment of the invention the sample is selected from the group comprising whole blood, plasma, and serum.

Mean arterial pressure (MAP) is defined as the average pressure in a patient's arteries during one cardiac cycle. It is considered as indicator of perfusion to vital organs. It is believed that a MAP that is greater than 70 mmHg is enough to sustain the organs of the average person. In the context of the present invention the term "mean arterial pressure is decreased" means a MAP below 75 mmHg.

The mature adrenomedullin peptide is an amidated peptide ($ADM-NH_2$), which comprises 52 amino acids (SEQ ID No: 1) and which comprises the amino acids 95 to 146 of pre-proADM 1-146, from which it is formed by proteolytic cleavage. Mature ADM, bio-ADM and $ADM-NH_2$ is used synonymously throughout this application and is a molecule according to SEQ ID No.: 1.

Another embodiment of the invention relates to an anti-ADM antibody or an anti-ADM antibody fragment or anti-ADM non-Ig scaffold for use in therapy or prevention of symptoms of illness selected from the group of nausea, headache, muscle aches, back pain, shivering, vomiting or for the use in therapy or prevention of illnesses characterized by such symptoms, such as migraine, in a subject in need thereof according to the preceding embodiment, wherein said antibody or fragment or scaffold binds to the N-terminal part (aa 1-21) of ADM:

(SEQ ID No. 4)
YRQSMNNFQGLRSFGCRFGTC.

Another embodiment of the invention relates to an anti-ADM antibody or an anti-ADM antibody fragment binding to ADM or anti-ADM non-Ig scaffold binding to ADM for use in therapy or prevention of symptoms of illness selected from the group of nausea, headache, muscle aches, back pain, shivering, vomiting or for the use in therapy or prevention of illnesses characterized by such symptoms, such as migraine, in a subject in need thereof according to any of the preceding embodiments as appropriate, characterized in that said antibody, antibody fragment or non-Ig scaffold bind to the to the midregional part, aa 21-42, of adrenomedullin:

(SEQ ID No. 3)
CTVQKLAHQIYQFTDKDKDNVA

Another embodiment of the invention relates to an anti-ADM antibody or an anti-ADM antibody fragment or anti-ADM non-Ig scaffold for use in therapy or prevention of symptoms of illness selected from the group of nausea, headache, muscle aches, back pain, shivering, vomiting or for the use in therapy or prevention of illnesses characterized by such symptoms, such as migraine, in a subject in need thereof according to any of the preceding embodiments, wherein said antibody or antibody fragment or non-Ig scaffold is monospecific, in particular monoclonal.

Another embodiment of the invention relates to an anti-ADM antibody or an anti-ADM antibody fragment or anti-ADM non-Ig scaffold for use in therapy or prevention of symptoms of illness selected from the group of nausea, headache, muscle aches, back pain, shivering, vomiting or for the use in therapy or prevention of illnesses characterized by such symptoms, such as migraine, in a subject in need thereof according to any of the preceding embodiments, wherein said antibody or fragment or scaffold exhibits a binding affinity to ADM of at least $10^{-7}$ M by label-free surface plasmon resonance using a Biacore 2000 system.

Another embodiment of the invention relates to anti-ADM antibody or an anti-ADM antibody fragment or anti-ADM non-Ig scaffold for use in therapy or prevention of symptoms of illness selected from the group of nausea, headache, muscle aches, back pain, shivering, vomiting in or for the use in therapy or prevention of illnesses characterized by such symptoms, such as migraine, a subject in need thereof according to any of the preceding embodiments, wherein said antibody or fragment or scaffold is not ADM-binding-Protein-1 (complement factor H).

Another embodiment of the invention relates to an anti-ADM antibody or an anti-ADM antibody fragment or anti-ADM non-Ig scaffold for use in therapy or prevention of symptoms of illness selected from the group of nausea, headache, muscle aches, back pain, shivering, vomiting or for the use in therapy or prevention of illnesses characterized by such symptoms, such as migraine, in a subject in need thereof according to any of the preceding embodiments, wherein said antibody or fragment or scaffold recognizes and binds to the N-terminal end (aa 1) of ADM.

Another embodiment of the invention relates to an anti-ADM antibody or an anti-ADM antibody fragment or anti-ADM non-Ig scaffold for use in therapy or prevention of symptoms of illness selected from the group of nausea, headache, muscle aches, back pain, shivering, vomiting or for the use in therapy or prevention of illnesses characterized by such symptoms, such as migraine, in a subject in need thereof according to any of the preceding embodiments, wherein said antibody or fragment or scaffold is an ADM stabilizing antibody or fragment or scaffold that enhances the half-life ($t_{1/2}$ half retention time) of ADM in serum, blood, plasma at least 10%, preferably at least, 50%, more preferably >50%, most preferably >100%.

Another embodiment of the invention relates to an anti-ADM antibody or an anti-ADM antibody fragment or anti-ADM non-Ig scaffold for use in therapy or prevention of symptoms of illness selected from the group of nausea, headache, muscle aches, back pain, shivering, vomiting or for the use in therapy or prevention of illnesses characterized by such symptoms, such as migraine, in a subject in need thereof according to any of the preceding embodiments, wherein said antibody or fragment or scaffold blocks the bioactivity of ADM not more than 80%, preferably not more than 50% using hADM 22-52 as a reference antagonist in CHO-K1 cells expressing human recombinant ADM receptor.

Another embodiment of the invention relates to an anti-ADM antibody or an anti-ADM antibody fragment or anti-ADM non-Ig scaffold for use in therapy or prevention of symptoms of illness selected from the group of nausea, headache, muscle aches, back pain, shivering, vomiting or for the use in therapy or prevention of illnesses characterized by such symptoms in a subject according to any of the preceding embodiments, wherein said subject in need thereof, is selected from the group of subjects suffering from a disease selected from the group comprising migraine, viral infections, drug-induced symptoms of disease (e.g., chemotherapy-induced, or induced by treatment with biologicals, antibiotics, anti-viral compounds, etc.). In a particular embodiment, the disease or illness (these terms may be used interchangeably) is migraine.

Another embodiment of the invention relates to an anti-ADM antibody or an anti-ADM antibody fragment or anti-ADM non-Ig scaffold for use in therapy or prevention of symptoms of illness selected from the group of nausea, headache, muscle aches, back pain, shivering, vomiting in a subject according to any of the preceding embodiments, wherein said subjects undergoes cancer therapy (chemotherapy).

Chemotherapy is a category of cancer treatment that uses one or more anti-cancer drugs (chemotherapeutic agents) as part of a standardized chemotherapy regimen. Chemotherapeutic drugs may include the following drug categories: alkylating agents, kinase inhibitors, vinca alkaloids, anthracyclines, antimetabolites, aromatase inhibitors, topoisomerase inhibitors, engineered anti-cancer agents such as monoclonal antibodies, cytokines, gene therapy vectors, antisense and peptide molecules.

Another embodiment of the invention relates to an anti-ADM antibody or an anti-ADM antibody fragment or anti-ADM non-Ig scaffold for use in therapy or prevention of symptoms of illness selected from the group of nausea, headache, muscle aches, back pain, shivering, vomiting or for the use in therapy or prevention of illnesses characterized by such symptoms, such as migraine, in a subject according to any of the preceding embodiments, wherein said antibody or fragment is a human monoclonal antibody or fragment that binds to the N-terminal region (aa 1-21) of ADM (SEQ ID No. 4) or an antibody fragment thereof wherein the heavy chain comprises the sequences:

CDR1:
SEQ ID NO: 5
GYTFSRYW

CDR2:
SEQ ID NO: 6
ILPGSGST

CDR3:
SEQ ID NO: 7
TEGYEYDGFDY and wherein the light chain comprises the sequences:

CDR1:
SEQ ID NO: 8
QSIVYSNGNTY

CDR2:
RVS

CDR3:
SEQ ID NO: 9
FQGSHIPYT.

Another embodiment of the invention relates to a human monoclonal antibody or fragment that binds to ADM or an antibody fragment thereof for use in therapy or prevention of symptoms of illness selected from the group of nausea, headache, muscle aches, back pain, shivering, vomiting or for the use in therapy or prevention of illnesses characterized by such symptoms, such as migraine, in a subject according to any of the preceding embodiments, wherein said antibody or fragment comprises a sequence selected from the group comprising as a VH region:

(AM-VH-C)
SEQ ID NO: 10
QVQLQQSGAELMKPGASVKISCKATGYTFSRYWIEWVKQRPGHGLEWIGEI
LPGSGSTNYNEKFKGKATITADTSSNTAYMQLSSLTSEDSAVYYCTEGYEY
DGFDYWGQGTTLTVSSASTKGPSVFPLAPSSKSTSGGTAALGCLVKDYFPE
PVTVSWNSGALTSGVHTFPAVLQSSGLYSLSSVVTVPSSSLGTQTYICNVN
HKPSNTKVDKRVEPKHHHHHH (AM-VH1)
SEQ ID NO: 11
QVQLVQSGAEVKKPGSSVKVSCKASGYTFSRYWISWVRQAPGQGLEWMGRI
LPGSGSTNYAQKFQGRVTITADESTSTAYMELSSLRSEDTAVYYCTEGYEY
DGFDYWGQGTTVTVSSASTKGPSVFPLAPSSKSTSGGTAALGCLVKDYFPE
PVTVSWNSGALTSGVHTFPAVLQSSGLYSLSSVVTVPSSSLGTQTYICNVN
HKPSNTKVDKRVEPKHHHHHH (AM-VH2-E40)
SEQ ID NO: 12
QVQLVQSGAEVKKPGSSVKVSCKASGYTFSRYWIEWVRQAPGQGLEWMGRI
LPGSGSTNYAQKFQGRVTITADESTSTAYMELSS LRSEDTAVYYCTEGYE
YDGFDYWGQGTTVTVSSASTKGPSVFPLAPSSKSTS GGTAALGCLVKDYF
PEPVTVSWNSGALTSGVHTFPAVLQSSGLYSLSSVVTVPSSSLGTQTYICN
VNHKPSNTKVDKRVEPKHHHHHH

-continued (AM-VH3-T26-E55)
SEQ ID NO: 13
QVQLVQSGAEVKKPGSSVKVSCKATGYTFSRYWISWVRQAPGQGLEWMGEI
LPGSGSTNYAQKFQGRVTITADESTSTAYMELSSLRSEDTAVYYCTEGYEY
DGFDYWGQGTTVTVSSASTKGPSVFPLAPSSKSTSGGTAALGCLVKDYFPE
PVTVSWNSGALTSGVHTFPAVLQSSGLYSLSSVVTVPSSSLGTQTYICNVN
HKPSNTKVDKRVEPKHHHHHH (AM-VH4-T26-E40-E55)
SEQ ID NO: 14
QVQLVQSGAEVKKPGSSVKVSCKATGYTFSRYWIEWVRQAPGQGLEWMGEI
LPGSGSTNYAQKFQGRVTITADESTSTAYMELSSLRSEDTAVYYCTEGYEY
DGFDYWGQGTTVTVSSASTKGPSVFPLAPSSKSTSGGTAALGCLVKDYFPE
PVTVSWNSGALTSGVHTFPAVLQSSGLYSLSSVVTVPSSSLGTQTYICNVN
HKPSNTKVDKRVEPKHHHHHH and comprises the following sequence as a VL region:

(AM-VL-C)
SEQ ID NO: 15
DVLLSQTPLSLPVSLGDQATISCRSSQSIVYSNGNTYLEWYLQKPGQSPKL
LIYRVSNRFSGVPDRFSGSGSGTDFTLKISRVEAEDLGVYYCFQGSHIPYT
FGGGTKLEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQ
GLSSPVTKSFNRGEC (AM-VL1)
SEQ ID NO: 16
DVVMTQSPLSLPVTLGQPASISCRSSQSIVYSNGNTYLNWFQQRPGQSPRR
LIYRVSNRDSGVPDRFSGSGSGTDFTLKISRVEAEDVGVYYCFQGSHIPYT
FGQGTKLEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQ
GLSSPVTKSFNRGEC (AM-VL2-E40)
SEQ ID NO: 17
DVVMTQSPLSLPVTLGQPASISCRSSQSIVYSNGNTYLEWFQQRPGQSPRR
LIYRVSNRDSGVPDRFSGSGSGTDFTLKISRVEAEDVGVYYCFQGSHIPYT
FGQGTKLEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQ
GLSSPVTKSFNRGEC

Another embodiment of the invention relates to a human monoclonal antibody or fragment that binds to ADM or an antibody fragment thereof for use in therapy or prevention of symptoms of illness selected from the group of nausea, headache, muscle aches, back pain, shivering, vomiting or for the use in therapy or prevention of illnesses characterized by such symptoms, such as migraine, in a subject according to any of the preceding embodiments, wherein said antibody or fragment comprises the following sequence as a heavy chain:

SEQ ID NO: 22

QVQLVQSGAEVKKPGSSVKVSCKASGYTFSRYWIEWVRQAPGQGLEWIGEI

LPGSGSTNYNQKFQGRVTITADTSTSTAYMELSSLRSEDTAVYYCTEGYEY

DGFDYWGQGTTVTVSSASTKGPSVFPLAPSSKSTSGGTAALGCLVKDYFPE

PVTVSWNSGALTSGVHTFPAVLQSSGLYSLSSVVTVPSSSLGTQTYICNVN

HKPSNTKVDKKVEPKSCDKTHTCPPCPAPELLGGPSVFLFPPKPKDTLMIS

RTPEVTCVVVDVSHEDPEVKFNWYVDGVEVHNAKTKPREEQYNSTYRVVSV

LTVLHQDWLNGKEYKCKVSNKALPAPIEKTISKAKGQPREPQVYTLPPSRD

ELTKNQVSLTCLVKGFYPSDIAVEWESNGQPENNYKTTPPVLDSDGSFFLY

SKLTVDKSRWQQGNVFScSVMHEALHNHYTQKSLSLSPGK and comprises the following sequence as a light chain:

SEQ ID NO: 23

DVVLTQSPLSLPVTLGQPASISCRSSQSIVYSNGNTYLEWYLQRPGQSPRL

LIYRVSNRFSGVPDRFSGSGSGTDFTLKISRVEAEDVGVYYCFQGSHIPYT

FGGGTKLEIKRTVAAPSVFIFPPSDEQLKSGTASVVCLLNNFYPREAKVQW

KVDNALQSGNSQESVTEQDSKDSTYSLSSTLTLSKADYEKHKVYACEVTHQ

GLSSPVTKSFNRGEC

In a specific embodiment of the invention the antibody comprises the following sequence as a heavy chain:

SEQ ID NO: 22

QVQLVQSGAEVKKPGSSVKVSCKASGYTFSRYWIEWVRQAPGQGLEWIGEI

LPGSGSTNYNQKFQGRVTITADTSTSTAYMELSSLRSEDTAVYYCTEGYEY

DGIDYWGQGTTVTVSSASTKGPSVFPLAPSSKSTSGGTAALGCLVKDYFPE

PVTVSWNSGALTSGVHTFPAVLQSSGLYSLSSVVTVPSSSLGTQTYICNVN

HKPSNTKVDKKVEPKSCDKTHTCPPCPAPELLGGPSVFLFPPKPKDTLMIS

RTPEVTCVVVDVSHEDPEVKFNWYVDGVEVHNAKTKPREEQYNSTYRVVSV

LTVLHQDWLNGKEYKCKVSNKALPAPIEKTISKAKGQPREPQVYTLPPSRD

ELTKNQVSLTCLVKGFYPSDIAVEWESNGQPENNYKTTPPVLDSDGSFFLY

SKLTVDKSRWQQGNVFSCSVMHEALHNHYTQKSLSLSPGK or a sequence that is >95% identical to it, preferably >98%, preferably >99% and comprises the following sequence as a light chain:

SEQ ID NO: 23

DVVLTQSPLSLPVTLGQPASISCRSSQSIVYSNGNTYLEWYLQRPGQSPRL

LIYRVSNRFSGVPDRFSGSGSGTDFTLKISRVEAEDVGVYYCFQGSHIPYT

FGGGTKLEIKRTVAAPSVFIFPPSDEQLKSGTASVVCLLNNFYPREAKVQW

KVDNALQSGNSQESVTEQDSKDSTYSLSSTLTLSKADYEKHKVYACEVTHQ

GLSSPVTKSFNRGEC or a sequence that is >95% identical to it, preferably >98%, preferably >99%.

To assess the identity between two amino acid sequences, a pairwise alignment is performed. Identity defines the percentage of amino acids with a direct match in the alignment.

Pharmaceutical composition comprising an antibody according as above outlined.

Another embodiment of the invention relates to an anti-ADM antibody or an anti-ADM antibody fragment or anti-ADM non-Ig scaffold for use in therapy or prevention of symptoms of illness selected from the group of nausea, headache, muscle aches, back pain, shivering, vomiting or for the use in therapy or prevention of illnesses characterized by such symptoms, such as migraine, in a subject in need thereof according to any of the preceding embodiments to be used in combination with known medicaments against nausea.

Another embodiment of the invention relates to an anti-ADM antibody or an anti-ADM antibody fragment or anti-ADM non-Ig scaffold for use in therapy or prevention of symptoms of illness selected from the group of nausea, headache, muscle aches, back pain, shivering, vomiting or for the use in therapy or prevention of illnesses characterized by such symptoms, such as migraine, in a subject in need thereof according to any of the preceding embodiments to be used in combination with known medicaments against headache.

Another embodiment of the invention relates to an anti-ADM antibody or an anti-ADM antibody fragment or anti-ADM non-Ig scaffold for use in therapy or prevention of symptoms of illness selected from the group of nausea, headache, muscle aches, back pain, shivering, vomiting or for the use in therapy or prevention of illnesses characterized by such symptoms, such as migraine, in a subject in need thereof according to any of the preceding embodiments to be used in combination with known medicaments against myalgia.

Another embodiment of the invention relates to an anti-ADM antibody or an anti-ADM antibody fragment or anti-ADM non-Ig scaffold for use in therapy or prevention of symptoms of illness selected from the group of nausea, headache, muscle aches, back pain, shivering, vomiting or for the use in therapy or prevention of illnesses characterized by such symptoms, such as migraine, in a subject in need thereof according to any of the preceding embodiments to be used in combination with known medicaments against shivering.

Another embodiment of the invention relates to an anti-ADM antibody or an anti-ADM antibody fragment or anti-ADM non-Ig scaffold for use in therapy or prevention of symptoms of illness selected from the group of nausea, headache, muscle aches, back pain, shivering, vomiting or for the use in therapy or prevention of illnesses characterized by such symptoms, such as migraine, in a subject in need thereof according to any of the preceding embodiments to be used in combination with known medicaments against vomiting.

Another embodiment of the invention relates to an anti-ADM antibody or an anti-ADM antibody fragment or anti-ADM non-Ig scaffold for use in therapy or prevention of symptoms of illness selected from the group of nausea, headache, muscle aches, back pain, shivering, vomiting or for the use in therapy or prevention of illnesses characterized by such symptoms, such as migraine, in a subject in need thereof according to any of the preceding embodiments to be used in combination with known medicaments against back pain.

Another embodiment of the invention relates to a pharmaceutical formulation for use in therapy or prevention of symptoms of illness selected from the group of nausea, headache, muscle aches, back pain, shivering, vomiting or for the use in therapy or prevention of illnesses characterized by such symptoms, such as migraine, in a subject in need thereof comprising an antibody or fragment or scaffold according to any of the preceding embodiments.

Another embodiment of the invention relates to a pharmaceutical formulation for use in therapy or prevention of symptoms of illness selected from the group of nausea, headache, muscle aches, back pain, shivering, vomiting or for the use in therapy or prevention of illnesses characterized by such symptoms, such as migraine, in a subject in need thereof according to the preceding embodiment, wherein said pharmaceutical formulation is a solution, preferably a ready-to-use solution.

Another embodiment of the invention relates to a pharmaceutical formulation for use in therapy or prevention of symptoms of illness selected from the group of nausea, headache, muscle aches, back pain, shivering, vomiting or for the use in therapy or prevention of illnesses characterized by such symptoms, such as migraine, in a subject according to the preceding embodiment, wherein said pharmaceutical formulation is in a freeze-dried state.

Another embodiment of the invention relates to a pharmaceutical formulation for use in therapy or prevention of symptoms of illness selected from the group of nausea, headache, muscle aches, back pain, shivering, vomiting or for the use in therapy or prevention of illnesses characterized by such symptoms, such as migraine, in a subject in need thereof according to any of the preceding embodiments relating to such formulations, wherein said pharmaceutical formulation is administered intra-muscular.

Another embodiment of the invention relates to a pharmaceutical formulation for use in therapy or prevention of symptoms of illness selected from the group of nausea, headache, muscle aches, back pain, shivering, vomiting or for the use in therapy or prevention of illnesses characterized by such symptoms, such as migraine, in a subject in need thereof according to any of the preceding embodiments relating to such formulations, wherein said pharmaceutical formulation is administered intra-vascular.

Another embodiment of the invention relates to a pharmaceutical formulation for use in therapy or prevention of symptoms of illness selected from the group of nausea, headache, muscle aches, back pain, shivering, vomiting or for the use in therapy or prevention of illnesses characterized by such symptoms, such as migraine, in a subject according to the preceding embodiment, wherein said pharmaceutical formulation is administered via infusion.

Another embodiment of the invention relates to a pharmaceutical formulation for use in therapy or prevention of symptoms of illness selected from the group of nausea, headache, muscle aches, back pain, shivering, vomiting or for the use in therapy or prevention of illnesses characterized by such symptoms, such as migraine, in a subject according to any of the according to any of the preceding embodiments relating to such formulations, wherein said pharmaceutical formulation is to be administered systemically.

As used herein, the definition of the "illness score" relates to LPS-induced clinical symptoms including nausea, headache, muscle aches, back pain, shivering, and vomiting. Those symptoms were combined into one score (=Illness score): as an example each symptom on a scale of 0 to 5, except vomiting (either 0 or 3, depending on having vomited in the previous 30 minutes). The Illness score is a sum over all symptoms (theoretical ranges from 0 to 28).

It should be emphasized that the herein described embodiments relating to anti-ADM antibody or an anti-ADM antibody fragment or anti-ADM non-Ig scaffold are intended to be applied for sake of therapy or prevention of symptoms associated with illnesses, and thus are not necessarily intended for any methods of primary treatment or first line treatment to the acute disease or acute condition itself that has to be considered as underlying disease(s). This means the present invention do not provide for a therapy of healing/curing e.g. cancer, sepsis, septic shock, COPD, congestive heart disease (acute heart failure).

Furthermore, in embodiments of the invention an anti-ADM antibody or an anti-ADM antibody fragment or an anti-ADM non-Ig scaffold is monospecific. Monospecific anti-ADM antibody or monospecific anti-ADM antibody fragment or monospecific anti-ADM non-Ig scaffold means that said antibody or antibody fragment or non-Ig scaffold binds to one specific region encompassing at least 5 amino acids within the target ADM. Monospecific anti-ADM antibody or monospecific anti-ADM antibody fragment or monospecific anti-ADM non-Ig scaffold are anti-ADM antibodies or anti-ADM antibody fragments or anti-ADM non-Ig scaffolds that all have affinity for the same antigen.

In a specific and preferred embodiment the present invention provides for a monospecific anti-ADM antibody or monospecific anti-ADM antibody fragment or monospecific anti-ADM non-Ig scaffold, characterized in that said antibody or antibody fragment or non-Ig scaffold binds to one specific region encompassing at least 4 amino acids within the target ADM. In another special embodiment the anti-ADM antibody or the antibody fragment binding to ADM is a monospecific antibody. Monospecific means that said antibody or antibody fragment binds to one specific region encompassing preferably at least 4, or at least 5 amino acids within the target ADM. Monospecific antibodies or fragments are antibodies or fragments that all have affinity for the same antigen. Monoclonal antibodies are monospecific, but monospecific antibodies may also be produced by other means than producing them from a common germ cell.

An antibody according to the present invention is a protein including one or more polypeptides substantially encoded by immunoglobulin genes that specifically binds an antigen. The recognized immunoglobulin genes include the kappa, lambda, alpha (IgA), gamma (IgG1, IgG2, IgG3, IgG4), delta (IgD), epsilon (IgE) and mu (IgM) constant region genes, as well as the myriad immunoglobulin variable region genes. Full-length immunoglobulin light chains are generally about 25 kDa or 214 amino acids in length. Full-length immunoglobulin heavy chains are generally about 50 kDa or 446 amino acid in length. Light chains are encoded by a variable region gene at the $NH_2$-terminus (about 110 amino acids in length) and a kappa or lambda constant region gene at the COOH—terminus. Heavy chains are similarly encoded by a variable region gene (about 116 amino acids in length) and one of the other constant region genes.

The basic structural unit of an antibody is generally a tetramer that consists of two identical pairs of immunoglobulin chains, each pair having one light and one heavy chain. In each pair, the light and heavy chain variable regions bind to an antigen, and the constant regions mediate effector functions Immunoglobulins also exist in a variety of other forms including, for example, Fv, Fab, and (Fab')2, as well as bifunctional hybrid antibodies and single chains (e.g., Lanzavecchia et al. 1987. *Eur. J. Immunol.* 17: 105; Huston et al 1988. *PNAS* 85:5879-5883; Bird et al. 1988. *Science* 242:423-426; Hood et al. 1984. *Immunology*, Benjamin, N.Y., 2nd ed.; Hunkapiller and Hood, 1986. *Nature* 323: 15-16). An immunoglobulin light or heavy chain variable region includes a framework region interrupted by three hypervariable regions, also called complementarity determining regions (CDR's) (see, Sequences of Proteins of Immunological Interest, E. Kabat et al, U.S. Department of Health and Human Services, 1983). As noted above, the CDRs are primarily responsible for binding to an epitope of an antigen. An immune complex is an antibody, such as a monoclonal antibody, chimeric antibody, humanized antibody or human antibody, or functional antibody fragment, specifically bound to the antigen.

Chimeric antibodies are antibodies whose light and heavy chain genes have been constructed, typically by genetic engineering, from immunoglobulin variable and constant region genes belonging to different species. For example, the variable segments of the genes from a mouse monoclonal antibody can be joined to human constant segments, such as kappa and gamma 1 or gamma 3. In one example, a therapeutic chimeric antibody is thus a hybrid protein composed of the variable or antigen-binding domain from a mouse antibody and the constant or effector domain from a human antibody, although other mammalian species can be used, or the variable region can be produced by molecular techniques. Methods of making chimeric antibodies are well known in the art, e.g., see U.S. Pat. No. 5,807,715. A "humanized" immunoglobulin is an immunoglobulin including a human framework region and one or more CDRs from a non-human (such as a mouse, rat, or synthetic) immunoglobulin. The non-human immunoglobulin providing the CDRs is termed a "donor" and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions, which have substantially no effect on antigen binding or other immunoglobulin functions. Exemplary conservative substitutions are those such as gly, ala; val, ile, leu; asp, glu; asn, gin; ser, thr; lys, arg; and phe, tyr. Humanized immunoglobulins can be constructed by means of genetic engineering (e.g., see U.S. Pat. No. 5,585,089). A human antibody is an antibody wherein the light and heavy chain genes are of human origin. Human antibodies can be generated using methods known in the art. Human antibodies can be produced by immortalizing a human B cell secreting the antibody of interest Immortalization can be accomplished, for example, by EBV infection or by fusing a human B cell with a myeloma or hybridoma cell to produce a trioma cell. Human antibodies can also be produced by phage display methods (see, e.g., Dower et al., PCT Publication No. WO 91/17271; McCafferty et al.; PCT Publication No. WO92/001047; and Winter, PCT Publication No. WO 92/20791), or selected from a human combinatorial monoclonal antibody library (see the Morphosys website). Human antibodies can also be prepared by using transgenic animals carrying a human immunoglobulin gene (for example, see PCT Publication No. WO 93/12227; and PCT Publication No. WO 91/10741).

Thus, the anti-ADM antibody may have the formats known in the art. Examples are human antibodies, monoclonal antibodies, humanized antibodies, chimeric antibodies, CDR-grafted antibodies. In a preferred embodiment antibodies according to the present invention are recombinantly produced antibodies as e.g. IgG, a typical full-length immunoglobulin, or antibody fragments containing at least the F-variable domain of heavy and/or light chain as e.g. chemically coupled antibodies (fragment antigen binding) including but not limited to Fab-fragments including Fab minibodies, single chain Fab antibody, monovalent Fab antibody with epitope tags, e.g. Fab-V5Sx2; bivalent Fab (mini-antibody) dimerized with the CH3 domain; bivalent Fab or multivalent Fab, e.g. formed via multirnerization with the aid of a heterologous domain, e.g. via dimerization of dHLX domains, e.g. Fab-dHLX-FSx2; F(ab')2-fragments, scFv-fragments, multimerized multivalent or/and multispecific scFv-fragments, bivalent and/or bispecific diabodies, BITE® (bispecific T-cell engager), trifunctional antibodies, polyvalent antibodies, e.g. from a different class than G; single-domain antibodies, e.g. nanobodies derived from camelid or fish immunoglobulins and numerous others.

In addition to anti-ADM antibodies other biopolymer scaffolds are well known in the art to complex a target molecule and have been used for the generation of highly target specific biopolymers. Examples are aptamers, spiegelmers, anticalins and conotoxins. For illustration of antibody formats please see FIGS. 1*a*, 1*b* and 1*c* in WO 2013/072513.

An antibody fragment according to the present invention is an antigen binding fragment of an antibody according to the present invention.

In a preferred embodiment the ADM antibody format is selected from the group comprising Fv fragment, scFv fragment, Fab fragment, scFab fragment, (Fab)2 fragment and scFv-Fc Fusion protein. In another preferred embodiment the antibody format is selected from the group comprising scFab fragment, Fab fragment, scFv fragment and bioavailability optimized conjugates thereof, such as PEGylated fragments. One of the most preferred formats is the scFab format.

Non-Ig scaffolds may be protein scaffolds and may be used as antibody mimics as they are capable to bind to ligands or antigens. Non-Ig scaffolds may be selected from the group comprising tetranectin-based non-Ig scaffolds (e.g. described in US 2010/0028995), fibronectin scaffolds (e.g. described in EP 1266 025; lipocalin-based scaffolds ((e.g. described in WO 201 1/154420); ubiquitin scaffolds (e.g. described in WO 2011/073214), transferring scaffolds (e.g. described in US 2004/0023334), protein A scaffolds (e.g. described in EP 2231860), ankyrin repeat based scaffolds (e.g. described in WO 2010/060748), microproteins preferably microproteins forming a cystine knot) scaffolds (e.g. described in EP 2314308), Fyn SH3 domain based scaffolds (e.g. described in WO 2011/023685) EGFR-A-domain based scaffolds (e.g. described in WO 2005/040229) and Kunitz domain based scaffolds (e.g. described in EP 1941867).

In one embodiment of the invention antibodies according to the present invention may be produced as follows: A Balb/c mouse was immunized with 100 μg ADM-Peptide-BSA-Conjugate at day 0 and 14 (emulsified in 100 μl complete Freund's adjuvant) and 50 μg at day 21 and 28 (in 100 μl incomplete Freund's adjuvant). Three days before the fusion experiment was performed, the animal received 50 μg of the conjugate dissolved in 100 μl saline, given as one intraperitoneal and one intravenous injection. Splenocytes from the immunized mouse and cells of the myeloma cell line SP2/0 were fused with 1 ml 50% polyethylene glycol for 30 s at 37° C. After washing, the cells were seeded in 96-well cell culture plates. Hybrid clones were selected by growing in HAT medium (RPMI 1640 culture medium supplemented with 20% fetal calf serum and HAT-Supplement). After two weeks the HAT medium is replaced with HT Medium for three passages followed by returning to the normal cell culture medium. The cell culture supernatants were primary screened for antigen specific IgG antibodies three weeks after fusion. The positive tested microcultures were transferred into 24-well plates for propagation. After retesting, the selected cultures were cloned and recloned using the limiting-dilution technique and the isotypes were determined (see also Lane, R. D. 1985. *J. Immunol. Meth.* 81: 223-228; Ziegler B. et al. 1996. *Horm. Metab. Res.* 28: 11-15).

Antibodies may also be produced by means of phage display according to the following procedure: The human naive antibody gene libraries HALT/8 were used for the isolation of recombinant single chain F-Variable domains (scFv) against ADM peptide. The antibody gene libraries were screened with a panning strategy comprising the use of peptides containing a biotin tag linked via two different spacers to the ADM peptide sequence. A mix of panning rounds using non-specifically bound antigen and streptavidin bound antigen were used to minimize background of non-specific binders. The eluted phages from the third round of panning have been used for the generation of monoclonal scFv expressing *E. coli* strains. Supernatants from the cultivation of these clonal strains have been directly used for an antigen ELISA testing (see references cited in WO 2013/072513, incorporated herein in their entirety).

Humanization of murine antibodies may be conducted according to the following procedure: For humanization of an antibody of murine origin the antibody sequence is analyzed for the structural interaction of framework regions (FR) with the complementary determining regions (CDR) and the antigen. Based on structural modelling an appropriate FR of human origin is selected and the murine CDR sequences are transplanted into the human FR. Variations in the amino acid sequence of the CDRs or FRs may be introduced to regain structural interactions, which were abolished by the species switch for the FR sequences. This recovery of structural interactions may be achieved by random approach using phage display libraries or via directed approach guided by molecular modeling (Almagro and Fransson 2008. *Front Biosci.* 13: 1619-33) in a preferred embodiment the ADM antibody format is selected from the group comprising Fv fragment, scFv fragment, Fab fragment, scFab fragment, F(ab)2 fragment and scFv-Fc Fusion protein. In another preferred embodiment the antibody format is selected from the group comprising scFab fragment, Fab fragment, scFv fragment and bioavailability optimized conjugates thereof, such as PEGylated fragments. One of the most preferred formats is scFab format. In another preferred embodiment, the anti-ADM antibody, anti-ADM antibody fragment, or anti-ADM non-Ig scaffold is a full length antibody, antibody fragment, or non-Ig scaffold.

In a preferred embodiment the anti-ADM antibody or an anti-ADM antibody fragment or anti-ADM non-Ig scaffold is directed to and can bind to an epitope of at least 5 amino acids in length contained in ADM.

In another preferred embodiment the anti-ADM antibody or an anti-ADM antibody fragment or anti-ADM non-Ig scaffold is directed to and can bind to an epitope of at least 4 amino acids in length contained in ADM.

In one specific embodiment of the invention the anti-ADM antibody or anti-ADM antibody fragment binding to ADM or anti-ADM non-Ig scaffold binding to ADM is provided for use in therapy of an acute disease or acute condition of a patient wherein said antibody or fragment or scaffold is not ADM-binding-Protein-1 (complement factor H). The acute disease or acute condition may be migraine.

In one specific embodiment of the invention the anti-ADM antibody or anti-ADM antibody fragment binding to ADM or anti-ADM non-Ig scaffold binding to ADM is provided for use in therapy of an acute disease or acute condition of a patient wherein said antibody or antibody fragment or non-Ig scaffold binds to a region of preferably at least 4, or at least 5 amino acids within the sequence of aa 1-42 of mature human ADM.

The above acute disease or acute condition may be headache, preferably a primary headache, most preferred migraine.

In one specific embodiment of the invention the anti-ADM antibody or anti-ADM antibody fragment binding to ADM or anti-ADM non-Ig scaffold binding to ADM is provided for use in therapy of an acute disease or acute condition of a patient wherein said antibody or fragment or scaffold binds to a region of preferably at least 4, or at least 5 amino acids within the sequence of aa 1-21 of mature human ADM:

```
                                   (SEQ ID NO.: 4)
YRQSMNNFQGLRSFGCRFGTC.
```

The above acute disease or acute condition may be migraine.

In a preferred embodiment of the present invention said anti-ADM antibody or an anti-ADM antibody fragment or anti-ADM non-Ig scaffold binds to a region of ADM that is located in the N-terminal part (amino acids 1-21) of ADM.

In another preferred embodiment said anti-ADM antibody or an anti-ADM antibody fragment or anti-ADM non-Ig scaffold recognizes and binds to the N-terminal end (aa1) of ADM. N-terminal end means that the amino acid 1, that is "Y" of SEQ ID No. 1 or 4 is mandatory for antibody binding. Said antibody or fragment or non-Ig scaffold would neither bind N-terminal extended nor N-terminally modified ADM nor N-terminally degraded ADM.

In a preferred embodiment the anti-ADM antibody or an anti-ADM antibody fragment or anti-ADM non-Ig scaffold is directed to and can bind to an epitope of at least 5 amino acids in length contained in ADM, preferably in human ADM.

In a preferred embodiment the anti-ADM antibody or an anti-ADM antibody fragment or anti-ADM non-Ig scaffold is directed to and can bind to an epitope of at least 4 amino acids in length contained in ADM, preferably in human ADM.

In one specific embodiment it is preferred to use an anti-ADM antibody or an anti-ADM antibody fragment or anti-ADM non-Ig scaffold according to the present invention, wherein said anti-ADM antibody or said anti-ADM antibody fragment or anti-ADM non-Ig scaffold is an ADM stabilizing antibody or an ADM stabilizing antibody fragment or an ADM stabilizing non-Ig scaffold that enhances the half-life ($t_{1/2}$; half retention time) of ADM in serum, blood, plasma at least 10%, preferably at least 50%, more preferably >50%, most preferably >100%. The half-life (half retention time) of ADM may be determined in human plasma in absence and presence of an ADM stabilizing antibody or an ADM stabilizing antibody fragment or an ADM stabilizing non-Ig scaffold, respectively, using an immunoassay for the quantification of ADM.

The following steps may be conducted:

ADM may be diluted in human citrate plasma in absence and presence of an ADM stabilizing antibody or an ADM stabilizing antibody fragment or an ADM stabilizing non-IG scaffold, respectively, and may be incubated at 24° C.;

Aliquots are taken at selected time points (e.g. within 24 hours) and degradation of ADM may be stopped in said aliquots by freezing at −20° C.;

The quantity of ADM may be determined by a hADM immunoassay directly, if the selected assay is not influenced by the stabilizing antibody. Alternatively, the aliquot may be treated with denaturing agents (like HCl) and, after clearing the sample (e.g. by centrifugation) the pH can be neutralized and the ADM-quantified by an ADM immunoassay. Alternatively, non-immunoassay technologies (e.g., RP-HPLC) can be used for ADM-quantification.

The half-life of ADM is calculated for ADM incubated in absence and presence of an ADM stabilizing antibody or an ADM stabilizing antibody fragment or an ADM stabilizing non-IG scaffold, respectively.

The enhancement of half-life is calculated for the stabilized ADM in comparison to ADM that has been incubated in absence of an ADM stabilizing antibody or an ADM stabilizing antibody fragment or an ADM stabilizing non-Ig scaffold.

A two-fold increase of the half-life of ADM is an enhancement of half-life of 100%. Half Life (half retention time) is defined as the period over which the concentration of a specified chemical or drug takes to fall to half baseline concentration in the specified fluid or blood.

In a specific embodiment said anti-ADM antibody, anti-ADM antibody fragment or anti-ADM non-Ig scaffold is a non-neutralizing antibody, fragment or non-Ig scaffold. A neutralizing anti-ADM antibody, anti-ADM antibody fragment or anti-ADM non-Ig scaffold would block the bioactivity of ADM to nearly 100%, to at least more than 90%, preferably to at least more than 95%.

In contrast, a non-neutralizing anti-ADM antibody, or anti-ADM antibody fragment or anti-ADM non-Ig scaffold blocks the bioactivity of ADM less than 100%, preferably to less than 95%, preferably to less than 90%, more preferred to less than 80% and even more preferred to less than 50%. This means that the residual bioactivity of ADM bound to the non-neutralizing anti-ADM antibody, or anti-ADM antibody fragment or anti-ADM non-Ig scaffold would be more than 0%, preferably more than 5%, preferably more than 10%, more preferred more than 20%, more preferred more than 50%. In this context (a) molecule(s), being it an antibody, or an antibody fragment or a non-Ig scaffold with "non-neutralizing anti-ADM activity", collectively termed here for simplicity as "non-neutralizing" anti-ADM antibody, antibody fragment, or non-Ig scaffold, that e.g. blocks the bioactivity of ADM to less than 80%, is defined as—a molecule or molecules binding to ADM, which upon addition to a culture of an eukaryotic cell line, which expresses functional human recombinant ADM receptor composed of CRLR (calcitonin receptor like receptor) and RAMP3 (receptor-activity modifying protein 3), reduces the amount of cAMP produced by the cell line through the action of parallel added human synthetic ADM peptide, wherein said added human synthetic ADM is added in an amount that in the absence of the non-neutralizing antibody to be analyzed, leads to half-maximal stimulation of cAMP synthesis, wherein the reduction of cAMP by said molecule(s) binding to ADM takes place to an extent, which is not more than 80%, even when the non-neutralizing molecule(s) binding to ADM to be analyzed is added in an amount, which is 10-fold more than the amount, which is needed to obtain the maximal reduction of cAMP synthesis obtainable with the non-neutralizing antibody to be analyzed. The same definition applies to the other ranges; 95%, 90%, 50% etc.

In a specific embodiment according to the present invention an anti-ADM antibody or an anti-ADM antibody fragment or anti-ADM non-Ig scaffold is used, wherein said antibody or antibody fragment or non-Ig scaffold blocks the bioactivity of ADM to less than 80%, preferably less than 50% (of baseline values). This is in the sense of blocking the circulating ADM of not more than 80% or not more than 50%, respectively. It has been understood that said limited blocking of the bioactivity of ADM occurs even at excess concentration of the antibody, antibody fragment or non-Ig scaffold, meaning an excess of the antibody, antibody fragment or non-Ig scaffold in relation to ADM. Said limited blocking is an intrinsic property of the ADM binder itself. This means that said antibody, antibody fragment or non-Ig scaffold have a maximal inhibition of 80% or 50%, respectively. By implication, this means that 20% or 50% residual ADM bioactivity remains present although appropriate amounts or excess amounts of antibody, antibody fragment or non-Ig scaffold are administered, respectively.

In a preferred embodiment said anti-ADM antibody, anti-ADM antibody fragment or anti-ADM non-Ig scaffold would block the bioactivity of ADM at least 5%. By implication, this means residual 95% circulating ADM bioactivity remains present. This is the lower threshold of bioactivity remaining after administration of said anti-ADM antibody, anti-ADM antibody fragment or anti-ADM non-Ig scaffold. The bioactivity is defined as the effect that a substance takes on a living organism or tissue or organ or functional unit in vivo or in vitro (e.g. in an assay) after its interaction. In case of ADM bioactivity this may be the effect of ADM in a human recombinant ADM receptor cAMP functional assay. Thus, according to the present invention bioactivity is defined via an ADM receptor cAMP functional assay. The following steps may be performed in order to determine the bioactivity of ADM in such an assay:

Dose response curves are performed with ADM in said human recombinant ADM receptor cAMP functional assay.

The ADM-concentration of half-maximal cAMP stimulation may be calculated.

At constant half-maximal cAMP-stimulating ADM-concentrations dose response curves (up to 100 μl final concentration) are performed by an ADM stabilizing antibody or an ADM stabilizing antibody fragment or an ADM stabilizing non-Ig scaffold, respectively.

A maximal (at maximal dose) inhibition by said ADM stabilizing antibody of 50% means that said ADM antibody or said ADM antibody fragment or said ADM non-Ig scaffold, respectively, blocks the bioactivity to 50% of baseline values. A maximal inhibition in said ADM bioassay of 80% means that said anti-ADM antibody or said anti-ADM antibody fragment or said anti-ADM non-Ig scaffold, respectively, blocks the bioactivity of ADM to 80%. This is in the sense of blocking the ADM bioactivity to not more than 80%.

In a preferred embodiment a modulating anti-ADM antibody or a modulating anti-ADM antibody fragment or a modulating anti-ADM non-Ig scaffold is used. A "modulating" anti-ADM antibody or a modulating anti-ADM antibody fragment or a modulating anti-ADM non-Ig scaffold is an antibody or an ADM antibody fragment or non-Ig scaffold that enhances the half-life (t half retention time) of ADM in serum, blood, plasma at least 10%, preferably at least, 50%, more preferably >50%, most preferably >100% and blocks the bioactivity of ADM to less than 80%, preferably less than 50% and wherein said anti-ADM antibody, anti-ADM antibody fragment or anti-ADM non-Ig scaffold would block the bioactivity of ADM at least 5%. These values related to half-life and blocking of bioactivity have to be understood in relation to the before-mentioned assays in order to determine these values. This is in the sense of blocking the circulating ADM of not more than 80% or not more than 50%, respectively. This means 20% residual ADM bioactivity remains present, or 50% residual ADM bioactivity remains present, respectively. Such a modulating anti-ADM antibody or a modulating anti-ADM antibody fragment or a modulating anti-ADM non-Ig scaffold offers the advantage that the dosing of the administration is facilitated. The combination of partially blocking or partially reducing ADM bioactivity and increase of the in vivo half-life (increasing the ADM bioactivity) leads to beneficial simplicity of anti-ADM antibody or an anti-ADM antibody fragment or anti-ADM non-Ig scaffold dosing. In a situation of excess endogenous ADM the activity lowering effect is the major impact of the antibody or fragment or scaffold, limiting the (negative) effect of ADM. In case of low or normal endogenous ADM concentrations, the biological effect of anti-ADM antibody or an anti-ADM antibody fragment or anti-ADM non-Ig scaffold is a combination of lowering (by partially blocking) and increase by increasing the ADM half-life. Thus, the non-neutralizing and modulating ADM antibody or ADM antibody fragment or ADM non-Ig scaffold acts like an ADM bioactivity buffer in order to keep the bioactivity of ADM within a certain physiological range.

The anti-ADM antibody or anti-ADM antibody fragment or anti-ADM non-Ig scaffold according to the present invention exhibits an affinity towards human ADM that the affinity constant is greater than $10^{-7}$ M, preferred $10^{-8}$ M, preferred affinity is greater than $10^{-9}$ M, most preferred higher than $10^{-10}$ M. A person skilled in the art knows that it may be considered to compensate lower affinity by applying a higher dose of compounds and this measure would not lead out-of-the-scope of the invention. The affinity constants may be determined according to the method as described in Example 1 of WO 2013/072513.

It should be emphasized that the term "ADM binding protein" comprises ADM-binding-protein-1 (complement factor H). However, said ADM binding protein by definition pursuant to the invention is neither a non-neutralizing anti-ADM antibody/antibody fragment/non-Ig scaffold nor a modulating anti-ADM antibody/antibody fragment/non-Ig scaffold. Subject of the present invention is further an anti-ADM antibody or an anti-ADM antibody fragment or anti-ADM non-Ig scaffold for use in therapy of acute disease or acute condition of a patient according to the present invention, wherein said antibody or antibody fragment or non-Ig scaffold may be used in combination with further active ingredients.

Subject of the present invention is further a pharmaceutical formulation comprising an anti-ADM antibody or anti-ADM antibody fragment or anti-ADM non-Ig scaffold according to the present invention. Subject of the present invention is further a pharmaceutical formulation according to the present invention wherein said pharmaceutical formulation is a solution, preferably a ready-to-use solution. In another embodiment subject of the present invention is further a pharmaceutical formulation according to the present invention wherein said pharmaceutical formulation is in a dried state to be reconstituted before use. Said pharmaceutical formulation may be administered intra-muscular. Said pharmaceutical formulation may be administered intravascular. Said pharmaceutical formulation may be administered via infusion. In another embodiment subject of the present invention is further a pharmaceutical formulation according to the present invention wherein said pharmaceutical formulation is in a freeze-dried state.

In another more preferred embodiment the present invention provides for a pharmaceutical formulation comprising an anti-ADM antibody or an anti-ADM antibody fragment binding to ADM or anti-ADM non-Ig scaffold binding to ADM for use in therapy or prevention of symptoms of illness in a patient, wherein said pharmaceutical formulation is to be administered to a patient in need thereof.

In another embodiment of the present invention the pharmaceutical formulation according to the present invention is to be administered to a patient for therapy and/or prevention of symptoms associated with illnesses as defined above with the proviso that said patient is in need of such treatment.

In one embodiment, the ADM antibody or an ADM antibody fragment or ADM non-IG scaffold according to the invention is a non-neutralizing ADM antibody or a non-neutralizing ADM antibody fragment or a non-neutralizing ADM non-Ig scaffold.

As used herein, the antibody format is selected from the group comprising Fv fragment, scFv fragment, Fab fragment, scFab fragment, (Fab)2 fragment and scFv-Fc Fusion protein.

In embodiments of the present invention, the ADM antibody or an ADM antibody fragment or non-Ig-scaffold according to any of the preceding embodiments for use in a treatment of a patient in need thereof wherein said antibody or fragment may be administered in a dose of at least 0.5 mg/Kg body weight, particularly at least 1.0 mg/kg body weight, more particularly, from 1.0 to 20.0 mg/kg body weight, e.g., from 2.0 to 10 mg/kg body weight, from 2.0 to 8.0 mg/kg body weight, or from 2.0 to 5.0 mg/kg body weight.

In embodiments of the present invention, the symptoms of illness referred to herein are not associated with either disease selected from the group comprising sepsis, diabetes, cancer, heart failure (acute heart failure), and septic shock.

In preferred embodiments of the present invention, the symptoms of illness that are treated or prevented using any of the ADM antibody or an ADM antibody fragment or non-Ig-scaffold according to any of preceding embodiments are associated with migraine.

In preferred embodiments of the present invention, the symptoms of illness that are treated or prevented using any of the ADM antibody or an ADM antibody fragment or non-Ig-scaffold according to any of preceding embodiments are associated with virus infections, wherein said viruses are selected from the group comprising hepadnaviridae, adenoviridae, herpesviridae, influenza viruses, arenaviridae, filoviridae, togaviridae, noroviruses, flaviviridae, retroviridae, measles virus, reoviridae, enteroviridae, picornaviridae, caliciviridae, etc.

In preferred embodiments of the present invention, the symptoms of illness that are treated or prevented using any of the ADM antibody or an ADM antibody fragment or non-Ig-scaffold according to any of preceding embodiments are associated with drug-treatment of primary diseases, such as chemotherapy, therapy with biologics (e.g., antibodies, or fragments thereof), antibiotics, or any medicaments causing any of the above mentioned symptoms of illness.

Further preferred embodiments of the present invention relate to methods of therapy (e.g., treatment, curing, alleviating, improving, amelioration, etc.) or prevention of symptoms as defined in any of the foregoing embodiments comprising administering to a subject in need thereof the ADM antibody or an ADM antibody fragment or non-Ig-scaffold according to any of preceding embodiments. The subject is preferably a human.

Administration of the ADM antibody or an ADM antibody fragment or non-Ig-scaffold can be by any means known in the art, including: orally, intravenously, subcutaneously, intraarterially, intramuscularly, intracardially, intraspinally, intrathoracically, intraperitoneal, intraventricular, sublingually, transdermal, and/or via inhalation. Administration may be systemic, e.g. intravenously, or localized.

In one aspect, the present invention provides a method for treating or preventing headache, preferably primary headache, more preferred migraine in an individual comprising administering to the individual an effective amount of an ADM antibody or an ADM antibody fragment or non-Ig-scaffold.

In a further embodiment, the invention provides methods for ameliorating, controlling, reducing incidence of, or delaying the development or progression of headache preferably primary headache, more preferred migraine in an individual comprising administering to the individual an effective amount of the ADM antibody or an ADM antibody fragment or non-Ig-scaffold.

The ADM antibody or an ADM antibody fragment or non-Ig-scaffold may be administered prior to, during and/or after headache. In some embodiments, the ADM antibody or an ADM antibody fragment or non-Ig-scaffold is administered prior to the attack of headache.

In some embodiments ADM antibody or an ADM antibody fragment or non-Ig-scaffold may be administered in conjunction with another agent, such as another agent for treating headache.

"Development" or "progression" of headache means initial manifestations and/or ensuing progression of the disorder. Development of headache can be detectable and assessed using standard clinical techniques as well known in the art. However, development also refers to progression that may be undetectable. For purpose of this invention, development or progression refers to the biological course of the symptoms. "Development" includes occurrence, recurrence, and onset. As used herein "onset" or "occurrence" of headache includes initial onset and/or recurrence.

As used herein, an "effective dosage" or "effective amount" of drug, compound, or pharmaceutical composition is an amount sufficient to effect beneficial or desired results. For prophylactic use, beneficial or desired results include results such as eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing pain intensity, duration, or frequency of headache attack, and decreasing one or more symptoms resulting from headache (biochemical, histological and/or behavioral), including its complications and intermediate pathological phenotypes presenting during development of the disease, increasing the quality of life of those suffering from the disease, decreasing the dose of other medications required to treat the disease, enhancing effect of another medication, and/or delaying the progression of the disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

The following embodiments are subject of the present invention:

1. Anti-adrenomedullin (ADM) antibody or an anti-adrenomedullin antibody fragment or anti-ADM non-Ig scaffold for use in therapy or prevention of symptoms of illness or for the use in therapy or prevention of an illness characterized by such symptoms in a subject in need thereof wherein said antibody or fragment or scaffold binds to ADM (1-52; SEQ ID NO: 1) or a fragment thereof.

2. Anti-adrenomedullin (ADM) antibody or an anti-adrenomedullin antibody fragment or anti-ADM non-Ig scaffold for use in therapy or prevention of symptoms of illness or for the use in therapy or prevention of an illness characterized by such symptoms in a subject in need thereof according to item 1, wherein said antibody or fragment or scaffold binds to the N-terminal part (aa 1-21) of ADM:

(SEQ ID No. 4)
YRQSMNNFQGLRSFGCRFGTC.

3. Anti-Adrenomedullin (ADM) antibody or an anti-ADM antibody fragment binding to ADM or anti-ADM non-Ig scaffold binding to adrenomedullin for use in therapy or prevention of symptoms of illness or for the use in therapy or prevention of an illness characterized by such symptoms in a subject in need thereof according to any of items 1 to 2, characterized in that said antibody, antibody fragment or non-Ig scaffold bind to the mid regional (MR-) portion of ADM, consisting of aa 21-42 of ADM:

(SEQ ID No. 3)
CTVQKLAHQIYQFTDKDKDNVA.

4. Anti-Adrenomedullin (ADM) antibody or an anti-ADM antibody fragment binding to ADM or anti-ADM non-Ig scaffold binding to adrenomedullin for use in therapy or prevention of symptoms of illness or for the use in therapy or prevention of an illness characterized by such symptoms in a subject in need thereof according to any of items 1 to 3, wherein the symptoms of illness are selected from the group of nausea, headache, muscle aches, back pain, shivering, and/or vomiting.

5. Anti-Adrenomedullin (ADM) antibody or an anti-ADM antibody fragment binding to ADM or anti-ADM non-Ig scaffold binding to adrenomedullin for use in therapy or prevention of symptoms of illness or for the use in therapy or prevention of an illness characterized by such symptoms according to any of items 1 to 4, wherein the illness is characterized by an amount of C-reactive protein (CRP) in a sample which is ≥10 mg/L, and/or wherein the amount of TNF in a sample is ≥50 pg/ml, and/or wherein the amount of bio-ADM in a sample which is ≥43 pg/ml, and/or wherein the mean arterial pressure in said subject in need thereof is decreased.

6. Anti-Adrenomedullin (ADM) antibody or an anti-ADM antibody fragment binding to ADM or anti-ADM non-Ig scaffold binding to adrenomedullin for use in therapy or prevention of symptoms of illness or for the use in therapy or prevention of an illness characterized by such symptoms in a subject in need thereof according to any of items 1 to 5, wherein the illnesses in a patient in need of therapy and/or prevention of such symptoms or illnesses are selected from the group of indications comprising inflammatory conditions, autoimmune diseases, metabolic diseases, brain diseases, cardiovascular diseases and drug-induced diseases.

7. Anti-Adrenomedullin (ADM) antibody or an anti-ADM antibody fragment binding to ADM or anti-ADM non-Ig scaffold binding to adrenomedullin for use in therapy or prevention of symptoms of illness or for the use in therapy or prevention of an illness characterized by such symptoms in a subject in need thereof according to any of items 1 to 5, wherein the illness is migraine.

8. Anti-adrenomedullin (ADM) antibody or an anti-adrenomedullin antibody fragment or anti-ADM non-Ig scaffold for use in therapy or prevention of symptoms of illness or for the use in therapy or prevention of an illness characterized by such symptoms in a subject in need thereof according to any one of items 1 to 7, wherein said antibody or antibody fragment or non-Ig scaffold is monospecific.

9. Anti-adrenomedullin (ADM) antibody or an anti-adrenomedullin antibody fragment or anti-ADM non-Ig scaffold for use in therapy or prevention of symptoms of illness or for the use in therapy or prevention of an illness characterized by such symptoms in a subject in need thereof according to any of items 1 to 8, wherein said antibody or fragment or scaffold exhibits a binding affinity to ADM of at least $10^{-7}$ M by label-free surface plasmon resonance using a Biacore 2000 system.

10. Anti-adrenomedullin (ADM) antibody or an anti-adrenomedullin antibody fragment or anti-ADM non-Ig scaffold for use in therapy or prevention of symptoms of illness or for the use in therapy or prevention of an illness characterized by such symptoms in a subject in need thereof according to any of items 1 to 9, wherein said antibody or fragment or scaffold is not ADM-binding-Protein-1 (complement factor H).

11. Anti-adrenomedullin (ADM) antibody or an anti-adrenomedullin antibody fragment or anti-ADM non-Ig scaffold for use in therapy or prevention of symptoms of illness or for the use in therapy or prevention of an illness characterized by such symptoms in a subject in need thereof according to any of the preceding claims, wherein said antibody or fragment or scaffold recognizes and binds to the N-terminal end (aa 1) of ADM.

12. Anti-adrenomedullin (ADM) antibody or an anti-adrenomedullin antibody fragment or anti-ADM non-Ig scaffold for use in therapy or prevention of symptoms of illness or for the use in therapy or prevention of an illness characterized by such symptoms in a subject in need thereof according to any of the preceding claims, wherein said antibody or fragment or scaffold is an ADM stabilizing antibody or fragment or scaffold that enhances the half-life (t½ half retention time) of ADM in serum, blood, plasma at least 10%, preferably at least, 50%, more preferably >50%, most preferably >100%.

13. Anti-adrenomedullin (ADM) antibody or an anti-adrenomedullin antibody fragment or anti-ADM non-Ig scaffold for use in therapy or prevention of symptoms of illness or for the use in therapy or prevention of an illness characterized by such symptoms in a subject in need thereof according to any of the preceding items, wherein said antibody or fragment or scaffold blocks the bioactivity of ADM not more than 80%, preferably not more than 50% using hADM 22-52 as a reference antagonist in CHO-K1 cells expressing human recombinant ADM receptor.

14. Anti-adrenomedullin (ADM) antibody or an anti-adrenomedullin antibody fragment or anti-ADM non-Ig scaffold for use in therapy or prevention of symptoms of illness or for the use in therapy or prevention of an illness characterized by such symptoms in a subject in need thereof according to any of the preceding items, wherein said subjects undergoes chemotherapy, treatment with biological biologics, antibiotics, or treatment with anti-viral compounds.

15. Anti-adrenomedullin (ADM) antibody or an anti-adrenomedullin antibody fragment or anti-ADM non-Ig scaffold for use in therapy or prevention of symptoms of illness or for the use in therapy or prevention of an illness characterized by such symptoms in a subject in need thereof according to any of the preceding items, wherein said antibody or fragment is a human monoclonal antibody or fragment that binds to ADM or an antibody fragment thereof wherein the heavy chain comprises the sequences:

```
CDR1:
                              SEQ ID NO: 5
GYTFSRYW

CDR2:
                              SEQ ID NO: 6
ILPGSGST

CDR3:
                              SEQ ID NO: 7
TEGYEYDGFDY
```

and wherein the light chain comprises the sequences:

```
CDR1:
                              SEQ ID NO: 8
QSIVYSNGNTY

CDR2:
RVS

CDR3:
                              SEQ ID NO: 9
FQGSHIPYT.
```

16. A human monoclonal antibody or fragment that binds to ADM or an antibody fragment thereof for use in therapy or prevention of symptoms of illness or for the use in therapy or prevention of an illness characterized by such symptoms in a subject according to item 15, wherein said antibody or fragment comprises a sequence selected from the group comprising as a VH region:

```
(AM-VH-C)
                                        SEQ ID NO: 10
QVQLQQSGAELMKPGASVKISCKATGYTFSRYWIEWVKQRPGHGLEWIGEI

LPGSGSTNYNEKFKGKATITADTSSNTAYMQLSSLTSEDSAVYYCTEGYEY

DGFDYWGQGTTLTVSSASTKGPSVFPLAPSSKSTSGGTAALGCLVKDYFPE
```

-continued

PVTVSWNSGALTSGVHTFPAVLQSSGLYSLSSVVTVPSSSLGTQTYICNVN

HKPSNTKVDKRVEPKHHHHHH (AM-VH1)
SEQ ID NO: 11
QVQLVQSGAEVKKPGSSVKVSCKASGYTFSRYWISWVRQAPGQGLEWMGRI

LPGSGSTNYAQKFQGRVTITADESTSTAYMELSSLRSEDTAVYYCTEGYEY

DGFDYWGQGTTVTVSSASTKGPSVFPLAPSSKSTSGGTAALGCLVKDYFPE

PVTVSWNSGALTSGVHTFPAVLQSSGLYSLSSVVTVPSSSLGTQTYICNVN

HKPSNTKVDKRVEPKHHHHHH (AM-VH2-E40)
SEQ ID NO: 12
QVQLVQSGAEVKKPGSSVKVSCKASGYTFSRYWIEWVRQAPGQGLEWMGRI

LPGSGSTNYAQKFQGRVTITADESTSTAYMELSSLRSEDTAVYYCTEGYEY

DGFDYWGQGTTVTVSSASTKGPSVFPLAPSSKSTSGGTAALGCLVKDYFPE

PVTVSWNSGALTSGVHTFPAVLQSSGLYSLSSVVTVPSSSLGTQTYICNVN

HKPSNTKVDKRVEPKHHHHHH (AM-VH3-T26-E55)
SEQ ID NO: 13
QVQLVQSGAEVKKPGSSVKVSCKATGYTFSRYWISWVRQAPGQGLEWMGEI

LPGSGSTNYAQKFQGRVTITADESTSTAYMELSSLRSEDTAVYYCTEGYEY

DGFDYWGQGTTVTVSSASTKGPSVFPLAPSSKSTSGGTAALGCLVKDYFPE

PVTVSWNSGALTSGVHTFPAVLQSSGLYSLSSVVTVPSSSLGTQTYICNVN

HKPSNTKVDKRVEPKHHHHHH (AM-VH4-T26-E40-E55)
SEQ ID NO: 14
QVQLVQSGAEVKKPGSSVKVSCKATGYTFSRYWIEWVRQAPGQGLEWMGEI

LPGSGSTNYAQKFQGRVTITADESTSTAYMELSSLRSEDTAVYYCTEGYEY

DGFDYWGQGTTVTVSSASTKGPSVFPLAPSSKSTSGGTAALGCLVKDYFPE

PVTVSWNSGALTSGVHTFPAVLQSSGLYSLSSVVTVPSSSLGTQTYICNVN

HKPSNTKVDKRVEPKHHHHHH and comprises a sequence selected from the group comprising the following sequence as a VL region:

(AM-VL-C)
SEQ ID NO: 15
DVLLSQTPLSLPVSLGDQATISCRSSQSIVYSNGNTYLEWYLQKPGQSPKL

LIYRVSNRFSGVPDRFSGSGSGTDFTLKISRVEAEDLGVYYCFQGSHIPYT

FGGGTKLEIKRTVAAPSVFIFPPSDEQLKSGTASVVCLLNNFYPREAKVQW

KVDNALQSGNSQESVTEQDSKDSTYSLSSTLTLSKADYEKHKVYACEVTHQ

GLSSPVTKSFNRGEC (AM-VL1)
SEQ ID NO: 16
DVVMTQSPLSLPVTLGQPASISCRSSQSIVYSNGNTYLNWFQQRPGQSPRR

LIYRVSNRDSGVPDRFSGSGSGTDFTLKISRVEAEDVGVYYCFQGSHIPYT

FGQGTKLEIKRTVAAPSVFIFPPSDEQLKSGTASVVCLLNNFYPREAKVQW

KVDNALQSGNSQESVTEQDSKDSTYSLSSTLTLSKADYEKHKVYACEVTHQ

GLSSPVTKSFNRGEC

-continued (AM-VL2-E40)
SEQ ID NO: 17
DVVMTQSPLSLPVTLGQPASISCRSSQSIVYSNGNTYLEWFQQRPGQSPRR

LIYRVSNRDSGVPDRFSGSGSGTDFTLKISRVEAEDVGVYYCFQGSHIPYT

FGQGTKLEIKRTVAAPSVFIFPPSDEQLKSGTASVVCLLNNFYPREAKVQW

KVDNALQSGNSQESVTEQDSKDSTYSLSSTLTLSKADYEKHKVYACEVTHQ

GLSSPVTKSFNRGEC.

17. A human monoclonal antibody or fragment that binds to ADM or an antibody fragment thereof for use in therapy or prevention of symptoms of illness or for the use in therapy or prevention of an illness characterized by such symptoms in a subject according to item 15, wherein said antibody or fragment comprises the following sequence as a heavy chain:

SEQ ID NO: 22
QVQLVQSGAEVKKPGSSVKVSCKASGYTFSRYWIEWVRQAPGQGLEWIGEI

LPGSGSTNYNQKFQGRVTITADTSTSTAYMELSSLRSEDTAVYYCTEGYEY

DGFDYWGQGTTVTVSSASTKGPSVFPLAPSSKSTSGGTAALGCLVKDYFPE

PVTVSWNSGALTSGVHTFPAVLQSSGLYSLSSVVTVPSSSLGTQTYICNVN

HKPSNTKVDKKVEPKSCDKTHTCPPCPAPELLGGPSVFLFPPKPKDTLMIS

RTPEVTCVVVDVSHEDPEVKFNWYVDGVEVHNAKTKPREEQYNSTYRVVSV

LTVLHQDWLNGKEYKCKVSNKALPAPIEKTISKAKGQPREPQVYTLPPSRD

ELTKNQVSLTCLVKGFYPSDIAVEWESNGQPENNYKTTPPVLDSDGSFFLY

SKLTVDKSRWQQGNVFSCSVMHEALHNHYTQKSLSLSPGK or a sequence that is >95% identical to it, and comprises the following sequence as a light chain:

SEQ ID NO: 23
DVVLTQSPLSLPVTLGQPASISCRSSQSIVYSNGNTYLEWYLQRPGQSPR

LLIYRVSNRFSGVPDRFSGSGSGTDFTLKISRVEAEDVGVYYCFQGSHIP

YTFGGGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC or a sequence that is >95% identical to it.

18. Pharmaceutical formulation for use in therapy or prevention of symptoms of illness or for the use in therapy or prevention of an illness characterized by such symptoms in a subject in need thereof comprising an antibody or fragment or scaffold according to any of items 1 to 17.

19. Antibody comprising the following sequences as a heavy chain:

SEQ ID NO: 22
QVQLVQSGAEVKKPGSSVKVSCKASGYTFSRYWIEWVRQAPGQGLEWIGE

ILPGSGSTNYNQKFQGRVTITADTSTSTAYMELSSLRSEDTAVYYCTEGY

EYDGFDYWGQGTTVTVSSASTKGPSVFPLAPSSKSTSGGTAALGCLVKDY

-continued

```
FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPGK
```

or a sequence that is >95% identical to it, preferably >98% and comprises the following sequence as a light chain:

```
                                             SEQ ID NO: 23
DVVLTQSPLSLPVTLGQPASISCRSSQSIVYSNGNTYLEWYLQRPGQSPR

LLIYRVSNRFSGVPDRFSGSGSGTDFTLKISRVEAEDVGVYYCFQGSHIP

YTFGGGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC
```

or a sequence that is >95% identical to it, preferably >98%.

20. Pharmaceutical composition comprising an antibody according to item 19.

EXAMPLES

Generation of Antibodies and Determination of their Affinity Constants

Several human and murine antibodies were produced and their affinity constants were determined (see Table 1).

Peptides/Conjugates for Immunization:

Peptides for immunization were synthesized, see Table 1, (JPT Technologies, Berlin, Germany) with an additional N-terminal Cysteine (if no Cysteine is present within the selected ADM-sequence) residue for conjugation of the peptides to Bovine Serum Albumin (BSA). The peptides were covalently linked to BSA by using Sulfolink-coupling gel (Perbio Science, Bonn, Germany). The coupling procedure was performed according to the manual of Perbio.

The murine antibodies were generated according to the following method:

A Balb/c mouse was immunized with 100 μg Peptide-BSA-Conjugate at day 0 and 14 (emulsified in 100 μl complete Freund's adjuvant) and 50 μg at day 21 and 28 (in 100 μl incomplete Freund's adjuvant). Three days before the fusion experiment was performed, the animal received 50 μg of the conjugate dissolved in 100 μl saline, given as one intraperitoneal and one intra-venous injection.

Splenocytes from the immunized mouse and cells of the myeloma cell line SP2/0 were fused with 1 ml 50% polyethylene glycol for 30 s at 37° C. After washing, the cells were seeded in 96-well cell culture plates. Hybrid clones were selected by growing in HAT medium (RPMI 1640 culture medium supplemented with 20% fetal calf serum and HAT-Supplement). After two weeks the HAT medium is replaced with HT Medium for three passages followed by returning to the normal cell culture medium.

The cell culture supernatants were primary screened for antigen specific IgG antibodies three weeks after fusion. The positive tested microcultures were transferred into 24-well plates for propagation. After retesting, the selected cultures were cloned and recloned using the limiting-dilution technique and the isotypes were determined (see also Lane, R. D. 1985. *J. Immunol. Meth.* 81: 223-228; Ziegler et al. 1996. *Horm. Metab. Res.* 28: 11-15).

Mouse Monoclonal Antibody Production:

Antibodies were produced via standard antibody production methods (Marx et al, 1997. *Monoclonal Antibody Production, ATLA* 25, 121) and purified via Protein A. The antibody purities were >95% based on SDS gel electrophoresis analysis.

Human Antibodies:

Human Antibodies were produced by means of phage display according to the following procedure:

The human naive antibody gene libraries HALT/8 were used for the isolation of recombinant single chain F-Variable domains (scFv) against ADM peptide. The antibody gene libraries were screened with a panning strategy comprising the use of peptides containing a biotin tag linked via two different spacers to the ADM peptide sequence. A mix of panning rounds using non-specifically bound antigen and streptavidin bound antigen were used to minimize background of non-specific binders. The eluted phages from the third round of panning have been used for the generation of monoclonal scFv expressing *E. coli* strains. Supernatant from the cultivation of these clonal strains has been directly used for an antigen ELISA testing (see also Hust et al. 2011. *Journal of Biotechnology* 152, 159-170; Schütte et al. 2009. *PLoS One* 4, e6625).

Positive clones have been selected based on positive ELISA signal for antigen and negative for streptavidin coated micro titer plates. For further characterizations the scFv open reading frame has been cloned into the expression plasmid pOPE107 (Hust et al. 2011. *Journal of Biotechnology* 152, 159-170), captured from the culture supernatant via immobilized metal ion affinity chromatography and purified by a size exclusion chromatography.

Affinity Constants:

To determine the affinity of the antibodies to ADM, the kinetics of binding of ADM to immobilized antibody was determined by means of label-free surface plasmon resonance using a Biacore 2000 system (GE Healthcare Europe GmbH, Freiburg, Germany). Reversible immobilization of the antibodies was performed using an anti-mouse Fc antibody covalently coupled in high density to a CM5 sensor surface according to the manufacturer's instructions (mouse antibody capture kit; GE Healthcare) (Lorenz et al. 2011. *Antimicrob Agents Chemother.* 55(1): 165-173).

The monoclonal antibodies were raised against the below depicted ADM regions of human and murine ADM, respectively. The following table represents a selection of obtained antibodies used in further experiments. Selection was based on target region:

TABLE 1

| Sequence Number | Antigen/Immunogen | ADM Region | Designation | Affinity constants Kd (M) |
|---|---|---|---|---|
| SEQ ID: 4 | YRQSMNNFQGLRSFGCRFGTC | 1-21 | NT-H | $5.9 \times 10^{-9}$ |
| SEQ ID: 21 | CTVQKLAHQIYQ | 21-32 | MR-H | $2 \times 10^{-9}$ |
| Amidated SEQ ID: 2 (with additional Cysteine at N-terminus | C-APRSKISPQGY-$NH_2$ | C-42-52 | CT-H | $1.1 \times 10^{-9}$ |
| SEQ ID: 18 | YRQSMNQGSRSNGCRFGTC | 1-19 | NT-M | $3.9 \times 10^{-9}$ |
| SEQ ID: 19 | CTFQKLAHQIYQ | 19-31 | MR-M | $4.5 \times 10^{-10}$ |
| Amidated SEQ ID: 20 (with additional Cysteine at N-terminus | C-APRNKISPQGY-$NH_2$ | C-40-50 | CT-M | $9 \times 10^{-9}$ |

Generation of Antibody Fragments by Enzymatic Digestion:

The generation of Fab and F(ab)2 fragments was done by enzymatic digestion of the murine full length antibody NT-M. Antibody NT-M was digested using a) the pepsin-based F(ab)2 Preparation Kit (Pierce 44988) and b) the papain-based Fab Preparation Kit (Pierce 44985). The fragmentation procedures were performed according to the instructions provided by the supplier. Digestion was carried out in case of F(ab)2-fragmentation for 8 h at 37° C. The Fab-fragmentation digestion was carried out for 16 h, respectively.

Procedure for Fab Generation and Purification:

The immobilized papain was equilibrated by washing the resin with 0.5 ml of Digestion Buffer and centrifuging the column at 5000×g for 1 minute. The buffer was discarded afterwards. The desalting column was prepared by removing the storage solution and washing it with digestion buffer, centrifuging it each time afterwards at 1000×g for 2 minutes. 0.5 ml of the prepared IgG sample where added to the spin column tube containing the equilibrated Immobilized Papain. Incubation time of the digestion reaction was done for 16 h on a tabletop rocker at 37° C. The column was centrifuged at 5000×g for 1 minute to separate digest from the Immobilized Papain. Afterwards the resin was washed with 0.5 ml PBS and centrifuged at 5000×g for 1 minute. The wash fraction was added to the digested antibody that the total sample volume was 1.0 ml. The NAb Protein A Column was equilibrated with PBS and IgG Elution Buffer at room temperature. The column was centrifuged for 1 minute to remove storage solution (contains 0.02% sodium azide) and equilibrated by adding 2 ml of PBS, centrifuge again for 1 minute and the flow-through discarded. The sample was applied to the column and resuspended by inversion. Incubation was done at room temperature with end-over-end mixing for 10 minutes. The column was centrifuged for 1 minute, saving the flow-through with the Fab fragments. (References: Coulter and Harris 1983. *J. Immunol. Meth.* 59, 199-203; Lindner et al. 2010. *Cancer Res.* 70, 277-87; Kaufmann et al. 2010. *PNAS.* 107, 18950-5; Chen et al. 2010. *PNAS.* 107, 14727-32; Uysal et al. 2009 *J. Exp. Med.* 206, 449-62; Thomas et al. 2009. *J. Exp. Med.* 206, 1913-27; Kong et al. 2009 *J. Cell Biol.* 185, 1275-840).

Procedure for Generation and Purification of F(ab')2 Fragments:

The immobilized Pepsin was equilibrated by washing the resin with 0.5 ml of Digestion Buffer and centrifuging the column at 5000×g for 1 minute. The buffer was discarded afterwards. The desalting column was prepared by removing the storage solution and washing it with digestion buffer, centrifuging it each time afterwards at 1000×g for 2 minutes. 0.5 ml of the prepared IgG sample where added to the spin column tube containing the equilibrated Immobilized Pepsin. Incubation time of the digestion reaction was done for 16 h on a tabletop rocker at 37° C. The column was centrifuged at 5000×g for 1 minute to separate digest from the Immobilized Papain. Afterwards the resin was washed with 0.5 mL PBS and centrifuged at 5000×g for 1 minute. The wash fraction was added to the digested antibody that the total sample volume was 1.0 ml. The NAb Protein A Column was equilibrated with PBS and IgG Elution Buffer at room temperature. The column was centrifuged for 1 minute to remove storage solution (contains 0.02% sodium azide) and equilibrated by adding 2 mL of PBS, centrifuge again for 1 minute and the flow-through discarded. The sample was applied to the column and resuspended by inversion. Incubation was done at room temperature with end-over-end mixing for 10 minutes. The column was centrifuged for 1 minute, saving the flow-through with the Fab fragments. (References: Mariani et al. 1991. *Mol. Immunol.* 28: 69-77; Beale 1987. *Exp Comp Immunol* 11:287-96; Ellerson et al. 1972. *FEBS Letters* 24(3):318-22; Kerbel and Elliot 1983. *Meth Enzymol* 93:113-147; Kulkarni et al. 1985. *Cancer Immunol Immunotherapy* 19:211-4; Lamoyi 1986. *Meth Enzymol* 121:652-663; Parham et al. 1982. *J Immunol Meth* 53:133-73; Raychaudhuri et al. 1985. *Mol Immunol* 22(9):1009-19; Rousseaux et al. 1980. *Mol Immunol* 17:469-82; Rousseaux et al. 1983. *J Immunol Meth* 64:141-6; Wilson et al. 1991. *J Immunol Meth* 138:111-9).

NT-H-Antibody Fragment Humanization:

The antibody fragment was humanized by the CDR-grafting method (Jones et al. 1986. *Nature* 321, 522-525).

The following steps where executed to achieve the humanized sequence:

Total RNA extraction: Total RNA was extracted from NT-H hybridomas using the Qiagen kit.

First-round RT-PCR: QIAGEN® OneStep RT-PCR Kit (Cat No. 210210) was used. RT-PCR was performed with primer sets specific for the heavy and light chains. For each RNA sample, 12 individual heavy chain and 11 light chain RT-PCR reactions were set up using degenerate forward primer mixtures covering the leader sequences of variable regions. Reverse primers are located in the constant regions of heavy and light chains. No restriction sites were engineered into the primers.

Reaction Setup: 5×QIAGEN® OneStep RT-PCR Buffer 5.0 μl, dNTP Mix (containing 10 mM of each dNTP) 0.8 μl, Primer set 0.5 μl, QIAGEN® OneStep RT-PCR Enzyme Mix 0.8 μl, Template RNA 2.0 μl, RNase-free water to 20.0 μl, Total volume 20.0 μl PCR condition: Reverse transcription: 50° C., 30 min; Initial PCR activation: 95° C., 15 min Cycling: 20 cycles of 94° C., 25 sec; 54° C., 30 sec; 72° C., 30 sec; Final extension: 72° C., 10 min Second-round semi-nested PCR: The RT-PCR products from the first-round reactions were further amplified in the second-round PCR. 12 individual heavy chain and 11 light chain RT-PCR reactions were set up using semi-nested primer sets specific for antibody variable regions.

Reaction Setup: 2×PCR mix 10 μl; Primer set 2 μl; First-round PCR product 8 μl; Total volume 20 μl; Hybridoma Antibody Cloning Report PCR condition: Initial denaturing of 5 min at 95° C.; 25 cycles of 95° C. for 25 sec, 57° C. for 30 sec, 68° C. for 30 sec; Final extension is 10 min 68° C.

After PCR is finished, run PCR reaction samples onto agarose gel to visualize DNA fragments amplified. After sequencing more than 15 cloned DNA fragments amplified by nested RT-PCR, several mouse antibody heavy and light chains have been cloned and appear correct. Protein sequence alignment and CDR analysis identifies one heavy chain and one light chain. As the amino acids on positions 26, 40 and 55 in the variable heavy chain and amino acid on position 40 in the variable light are critical to the binding properties, they may be reverted to the murine original. The resulting candidates are depicted below. (Padlan 1991. *Mol. Immunol.* 28, 489-498; Harris and Bajorath. 1995. *Protein Sci.* 4, 306-310).

Annotation for the antibody fragment sequences (SEQ ID No.: 10 to 17): bold and underlined are the CDR 1, 2, 3 in numeric order from the N-terminus to the C-terminus; italic are constant regions; hinge regions are highlighted with bold, underlined letters and the histidine tag at the C-terminus with bold and italic letters.

(AM-VH-C)

SEQ ID No.: 10

QVQLQQSGAELMKPGASVKISCKATGYTFSRYWIEWVKQRPGHGLEWIGEILPGSG

STNYNEKFKGKATITADTSS*NTAYMQLSSLTSEDSAVYYC*_TEGYEYDGFDY_*WGQGTTLT*

*VSSASTKGPSVFPLAPSSKSTSGGTAALGCLVKDYFPEPVTVSWNSGALTSGVHTFPAVLQS*

*SGLYSLSSVVTVPSSSLGTQTYICNVNHKPSNTKVDKRV*__EPK__*HHHHHH*

(AM-VH1)

SEQ ID No.: 11

QVQLVQSGAEVKKPGSSVKVSCKASGYTFSRYWISWVRQAPGQGLEWMGRILPGS

GSTNYAQKFQGRVTITADE*STSTAYMELSSLRSEDTAVYYC*_TEGYEYDGFDY_*WGQGTTV*

*TVSSASTKGPSVFPLAPSSKSTSGGTAALGCLVKDYFPEPVTVSWNSGALTSGVHTFPAVLQ*

*SSGLYSLSSVVTVPSSSLGTQTYICNVNHKPSNTKVDKRV*__EPK__*HHHHHH*

(AM-VH2-E40)

SEQ ID No.: 12

QVQLVQSGAEVKKPGSSVKVSCKASGYTFSRYWIEWVRQAPGQGLEWMGRILPGS

GSTNYAQKFQGRVTITADE*STSTAYMELSSLRSEDTAVYYC*_TEGYEYDGFDY_*WGQGTTV*

*TVSSASTKGPSVFPLAPSSKSTSGGTAALGCLVKDYFPEPVTVSWNSGALTSGVHTFPAVLQ*

*SSGLYSLSSVVTVPSSSLGTQTYICNVNHKPSNTKVDKRV*__EPK__*HHHHHH*

(AM-VH3-T26-E55)

SEQ ID No.: 13

QVQLVQSGAEVKKPGSSVKVSCKATGYTFSRYWISWVRQAPGQGLEWMGEILPGS

GSTNYAQKFQGRVTITADE*STSTAYMELSSLRSEDTAVYYC*_TEGYEYDGFDY_*WGQGTTV*

*TVSSASTKGPSVFPLAPSSKSTSGGTAALGCLVKDYFPEPVTVSWNSGALTSGVHTFPAVLQ*

*SSGLYSLSSVVTVPSSSLGTQTYICNVNHKPSNTKVDKRV*__EPK__*HHHHHH*

(AM-VH4-T26-E40-E55)

SEQ ID No.: 14

QVQLVQSGAEVKKPGSSVKVSCKATGYTFSRYWIEWVRQAPGQGLEWMGEILPGS

GSTNYAQKFQGRVTITADE*STSTAYMELSSLRSEDTAVYYC*_TEGYEYDGFDY_*WGQGTTV*

-continued

*TVSSASTKGPSVFPLAPSSKSTSGGTAALGCLVKDYFPEPVTSWNSGALTSGVHTFPAVLQ*

*SSGLYSLSSVVTVPSSSLGTQTYICNVNHKPSNTKVDKRV*EPK*HHHHHH*

(AM-VL-C)

SEQ ID No.: 15

DVLLSQTPLSLPVSLGDQATISCRSSQSIVYSNGTYLEWYLQKPGQSPKLLIYRVSN

RFSGVPDRFSGSGSGTDFTLKISRVEAEDLGVYYCFQGSHIPYTFGGGTKLEIKRTVA

APSVFIFPPSDEQLKSGTASVVCLLNNFYPREAKVQWKVDNALQSGNSQESVTEQDS

KDSTYSLSSTLTLSKADYEKHKVYACEVTHQGLSSPVTKSFNRGEC (AM-VL1)

SEQ ID No.: 16

DVVMTQSPLSLPVTLGQPASISCRSSQSIVYSNGTYLNWFQQRPGQSPRRLIYRVSN

RDSGVPDRFSGSGSGTDFTLKISRVEAEDVGVYYCFQGSHIPYTFGQGTKLEIKRTVA

APSVFIFPPSDEQLKSGTASVVCLLNNFYPREAKVQWKVDNALQSGNSQESVTEQDS

KDSTYSLSSTLTLSKADYEKHKVYACEVTHQGLSSPVTKSFNRGEC (AM-VL2-E40)

SEQ ID No.: 17

DVVMTQSPLSLPVTLGQPASISCRSSQSIVYSNGTYLEWFQQRPGQSPRRLIYRVSN

RDSGVPDRFSGSGSGTDFTLKISRVEAEDVGVYYCFQGSHIPYTFGQGTKLEIKRTVA

APSVFIFPPSDEQLKSGTASVVCLLNNFYPREAKVQWKVDNALQSGNSQESVTEQDS

KDSTYSLSSTLTLSKADYEKHKVYACEVTHQGLSSPVTKSFNRGEC (Adrecizumab heavy chain)

SEQ ID NO: 22

QVQLVQSGAEVKKPGSSVKVSCKASGYTFSRYWIEWVRQAPGQGLEWIGEILPGSG

STNYNQKFQGRVTITADTSTSTAYMELSSLRSEDTAVYYCTEGYEYDGFDYWGQGT

TVTVSSASTKGPSVFPLAPSSKSTSGGTAALGCLVKDYFPEPVTVSWNSGALTSGVHT

FPAVLQSSGLYSLSSVVTVPSSSLGTQTYICNVNHKPSNTKVDKKVEPKSCDKTHTCP

PCPAPELLGGPSVFLFPPKPKDTLMISRTPEVTCVVVDVSHEDPEVKFNWYVDGVEV

HNAKTKPREEQYNSTYRVVSVLTVLHQDWLNGKEYKCKVSNKALPAPIEKTISKAK

GQPREPQVYTLPPSRDELTKNQVSLTCLVKGFYPSDIAVEWESNGQPENNYKTTPPVL

D SDGSFFLYSKLTVDKSRWQQGNVFSCSVMHEALHNHYTQKSLSLSPGK (Adrecizumab light chain)

SEQ ID NO: 23

DVVLTQSPLSLPVTLGQPASISCRSSQSIVYSNGTYLEWYLQRPGQSPRLLIYRVSN

RFSGVPDRFSGSGSGTDFTLKISRVEAEDVGVYYCFQGSHIPYTFGGGTKLEIKRTVA

APSVFIFPPSDEQLKSGTASVVCLLNNFYPREAKVQWKVDNALQSGNSQESVTEQDS

KDSTYSLSSTLTLSKADYEKHKVYACEVTHQGLSSPVTKSFNRGEC

Example 2—A Randomized Double-Blind Placebo-Controlled Phase I Study on the Safety, Tolerability and Pharmacokinetics/-Dynamics of Escalating Single Intravenous Doses of Anti-ADM-Antibody (ADRECIZUMAB) (HAM8101) in Healthy Male Subjects During Experimental Endotoxemia

Overall Trial Design

A randomized, double-blind, placebo-controlled phase I study in healthy male volunteers during experimental endotoxemia with single, escalating per group doses of Adrecizumab administered as i.v. infusion over a 1 hour period. A continuous LPS (lipopolysaccharide) model was used to induce experimental endotoxemia; administration of LPS in an initial bolus of 1 ng/kg followed by continuous infusion at 1 ng/kg/h for 3 hours. Subject will receive one course of treatment with study medication (Adrecizumab or placebo), 1 hour after start of LPS administration. The model of systemic inflammation has been recently described (Kiers et al. 2017. *Scientific Reports* 7: 40149).

Adrecizumab was administrated as single infusion over a 1 hour period in a dose of 0.5 mg/kg and was increased up to 2.0 and 8.0 mg/kg in subsequent treatment groups (see Table 2).

TABLE 2

| Study groups of 8 subjects received treatment by 1-hour infusion | | |
|---|---|---|
| Group | Treatment | |
| Group 1 | 0.5 mg/kg HAM8101 (n = 6) | Placebo (n = 2) |
| Group 2 | 2.0 mg/kg HAM8101 (n = 6) | Placebo (n = 2) |
| Group 3 | 8.0 mg/kg HAM8101 (n = 6) | Placebo (n = 2) |

Selection of Trial Population

The study population consisted of healthy young male volunteers. To be included into the trial, subjects had to meet all inclusion criteria and none of the exclusion criteria.

Inclusion Criteria

1. Written informed consent to participate in this trial prior to any study-mandated procedure.
2. Male subjects aged 18 to 35 years inclusive.
3. Subjects have to agree to use a reliable way of contraception with their partners from study entry until 3 months after study drug administration.
4. BMI between 18 and 30 kg/m$^2$, with a lower limit of body weight of 50 kg and an upper limit of 100 kg.
5. Healthy as determined by medical history, physical examination, vital signs, 12-lead electrocardiogram, and clinical laboratory parameters.

Exclusion Criteria

1. Unwillingness to abstain from any medication, recreational drugs or anti-oxidant vitamin supplements during the course of the study and within 7 days prior to the treatment day.
2. Unwillingness to abstain from smoking, or alcohol within 1 day prior to the treatment day.
3. Previous participation in a trial where LPS was administered.
4. Surgery or trauma with significant blood loss or blood donation within 3 months prior to the treatment day.
5. History, signs or symptoms of cardiovascular disease, in particular:
   - History of frequent vasovagal collapse or of orthostatic hypotension
   - Resting pulse rate ≤45 or ≥100 beats/min
   - Hypertension (RR systolic >160 or RR diastolic >90 mmHg)
   - Hypotension (RR systolic <100 or RR diastolic <50 mmHg)
   - Conduction abnormalities on the ECG consisting of a 1st degree atrioventricular block or a complex bundle branch block
   - Any chronic cardiac arrhythmias (except PAC's, PVC's)
6. Renal impairment: plasma creatinine >120 μmol/L
7. Liver function tests (alkaline phosphatase, AST, ALT and/or γ-GT) above 2× the upper limit of normal.
8. History of asthma
9. Atopic constitution
10. CRP above 2× the upper limit of normal, or clinically significant acute illness, including infections, within 2 weeks before the treatment day.
11. Treatment with investigational drugs or participation in any other clinical trial within 30 days prior to the Treatment day.
12. Known or suspected of not being able to comply with the trial protocol.
13. Known hypersensitivity to any excipients of the drug formulations used.
14. Inability to personally provide written informed consent (e.g. for linguistic or mental reasons) and/or take part in the study.

Lipopolysaccharide (LPS) from *Escherichia coli* Type O113

To achieve a controlled inflammatory state, subjects received lipopolysaccharide (LPS, U.S. reference endotoxin [*Escherichia coli* O:113, List Biological Laboratories Inc., Campbell, California, US]) intravenously.

Examination Hierarchy and Time Windows

The pre-dose blood samples were drawn on T=0 (baseline). Vital signs were measured after 5 min of resting in supine or semi-supine position. Schedule for blood samples and control visits (see table 2 for more detailed information):

- On the treatment day (Day 0), blood samples had to be taken at scheduled times ±5 min
- After 24 hours (Day 1), the follow-up visit and blood withdrawal had to be planned at ±1 hour after IMP administration.
- On day 7, the follow-up visit could be planned at any time, ±1 day.
- On day 14 and 28, the follow-up visit could be planned at any time, ±2 days.
- On day 60 and 90, the follow-up visit could be planned at any time, ±3 days.

Laboratory Monitoring

The following hematology parameters were analyzed: Hemoglobin, Hematocrit, RBC, MCV, MCH, MCHC, WBC, Platelets, Differential blood count.

Blood samples were collected in serum separation tubes and the following biochemistry parameters were analyzed: CRP, AF, ALT, AST, γ-GT, Creatine kinase, LDH, Urea-N, Creatinine, Sodium, Potassium, PT and APTT Primary endpoint variables are: Adverse Events; vital signs during the first 10 hours after Adrecizumab administration and at follow-up periods (T=24 hours, T=7 days, T=14 days, T=28 days, T=60 days, T=90 days), e.g. heart rate, blood pressure, oxygen saturation, temperature; Local tolerability at site of i.v. infusion; safety laboratory parameters (Hb, Ht, leukocytes, thrombocytes, leukocyte differential blood count, sodium, potassium, creatinine, urea, alkaline phosphatase, ALT, AST, GGT, CK, CRP, PT, APTT); 12-lead electrocardiogram (ECG), 2 and 8 hours after Adrecizumab administration.

Secondary endpoints are: Pharmacokinetics of Adrecizumab during experimental endotoxemia (including AUC, Cmax, Terminal T½, Cl, V); plasma levels of inflammatory mediators on the endotoxemia day (including but not limited to TNFα, IL-6, IL-8, IL-10); Symptom Illness score; Optional: Kidney damage markers (including but not limited to creatinine clearance, pro-Enkephalin and KIM-1).

TABLE 2

| baseline characteristics per group (mean ± SD) | | | | | |
|---|---|---|---|---|---|
| | Placebo | 0.5 mg/kg | 2.0 mg/kg | 8.0 mg/kg | P-value * |
| Age | 22.0 ± 1.1 | 22.0 ± 2.8 | 23.3 ± 2.5 | 22.5 ± 2.7 | 0.745 |
| BMI | 23.7 ± 1.3 | 23.3 ± 1.5 | 24.7 ± 1.9 | 25.6 ± 3.0 | 0.263 |

* Tested with one-way ANOVA

No Serious Adverse Events (SAEs) or Suspected Unsuspected Serious Adverse Reactions (SUSARs) were observed during the complete duration of the study, including the 90 day follow-up period.

Results

The Illness Score drops quicker under Adrecizumab treatment compared to placebo.

Both, 2 and 8 mg/kg have a significantly lower illness score than placebo between the time points at 210 min (T210) to 450 min (T450) (p=0.011 and 0.005, respectively; GLM repeated measures) (FIG. 1).

FIG. 2 shows the distribution of the illness scores by treatment arm at T270 (time point 270 min) and T300 (time point 300 min), respectively (FIGS. 2 A) and B)) supporting the surprisingly beneficial effect of the antibody of the present invention.

The contribution of single illness score components to the effect is illustrated in FIG. 3: A) nausea, B) headache, C) muscle aches, D) back pain, and E) shivering. All symptoms shown contribute significantly to the effect. Vomiting occurred only in two patients once each and could not be analyzed.

FIG. 4 shows an alternative evaluation. Here another score, the Sickness score was evaluated using the single question regarding the overall sickness, on a scale from 0 to 10. Again, the sickness score drops quicker in anti-ADM-antibody (Adrecizumab)-treated patients.

Administration of NT-H in Healthy Humans

The study was conducted in healthy male subjects as a randomized, double-blind, placebo-controlled, study with single escalating doses of NT-H antibody administered as intravenous (i.v.) infusion in 3 sequential groups of 8 healthy male subjects each (1st group 0.5 mg/kg, 2nd group 2 mg/kg, 3rd group 8 mg/kg) of healthy male subjects (n=6 active, n=2 placebo for each group).

The main inclusion criteria were written informed consent, age 18-35 years, agreement to use a reliable way of contraception and a BMI between 18 and 30 kg/$m^2$.

Subjects received a single i.v. dose of NT-H antibody (0.5 mg/kg; 2 mg/kg; 8 mg/kg) or placebo by slow infusion over a 1-hour period in a research unit.

The baseline ADM-values in the 4 groups did not differ. Median ADM values were 7.1 pg/mL in the placebo group, 6.8 pg/mL in the first treatment group (0.5 mg/kg), 5.5 pg/mL in second treatment group (2 mg/kg) and 7.1 pg/mL in the third treatment group (8 mg/mL).

The results show, that ADM-values rapidly increased within the first 1.5 hours after administration of NT-H antibody in healthy human individuals, then reached a plateau and slowly declined (FIG. 5).

Two subjects within the placebo group and 3 subjects in total from the treated group reported symptoms of migraine prior to receiving the single dose of placebo and NT-H antibody, respectively. After every time point symptoms were requested again. The subjects treated with NT-H antibody did not report any symptoms of migraine 4 hours after treatment, whereas the two subjects who received placebo still suffered from migraine symptoms as prior to the infusion.

---

SEQUENCE LISTING

Figure 1:
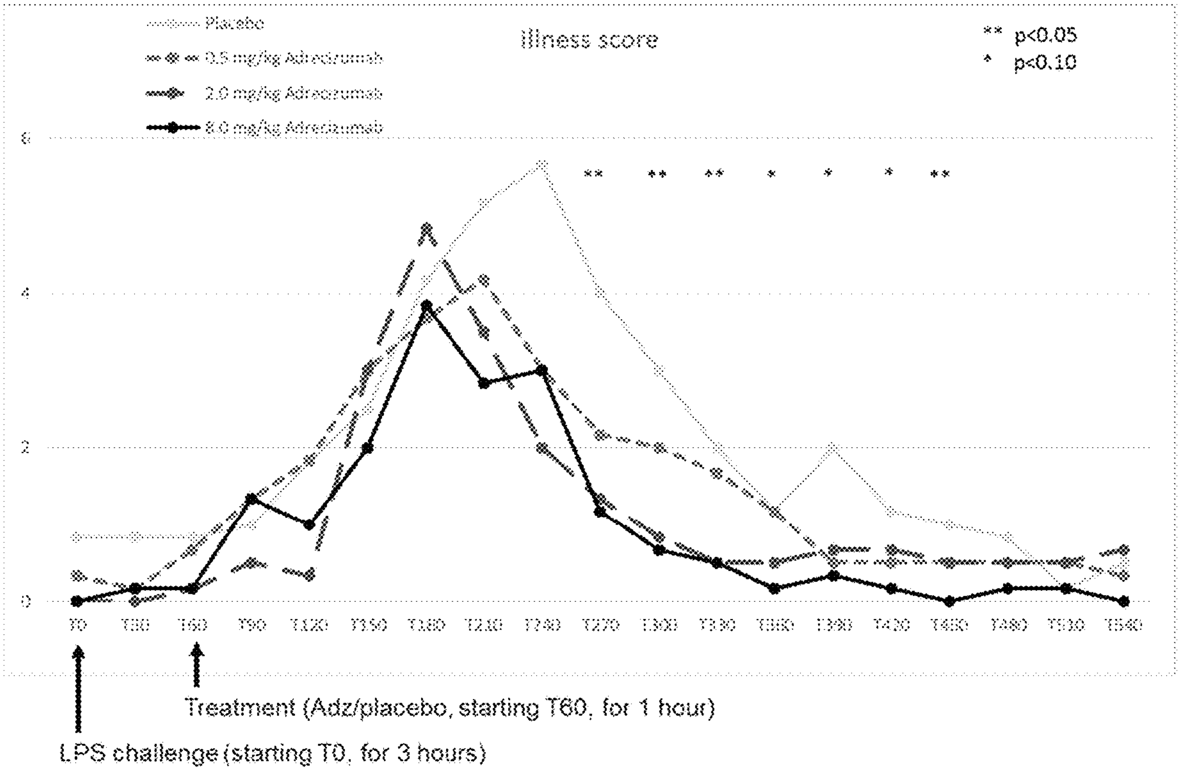
FIGS. 1, 2A, 2B, 3A, 3B, 3C, 3D, 3B, 4 and 5 are graphs.
Figure 2:
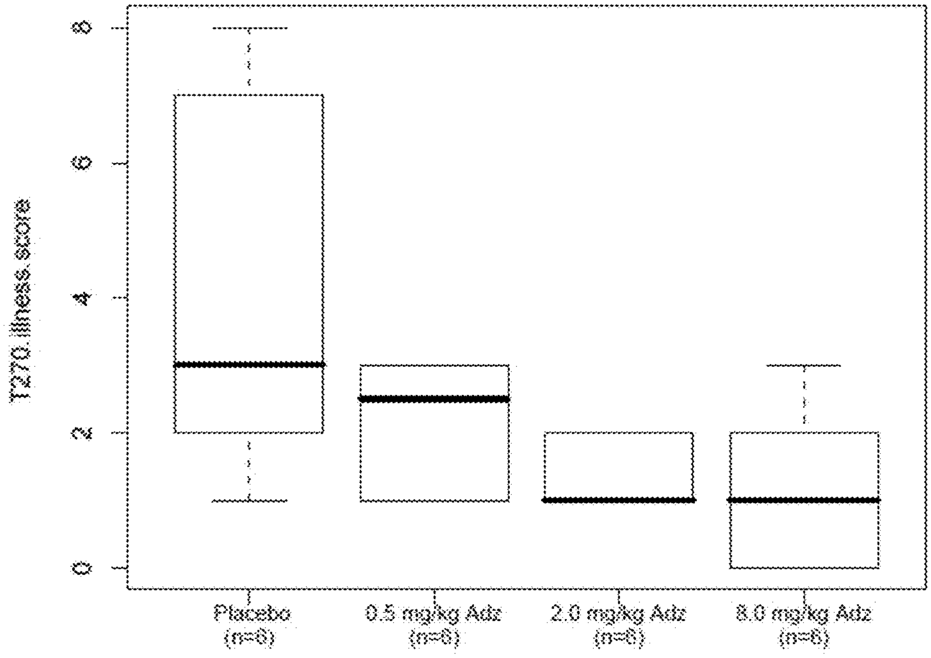
Figure 2:
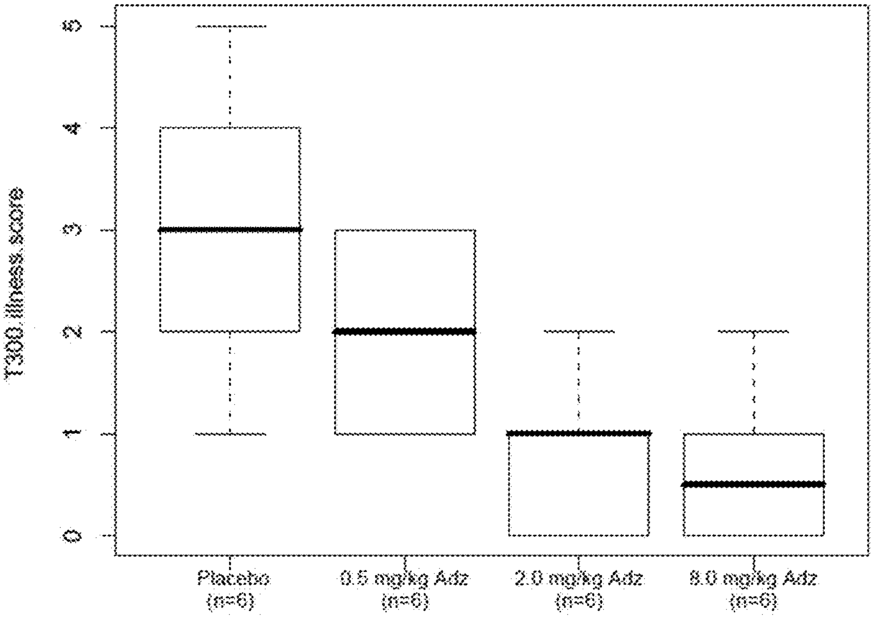
Figure 3:
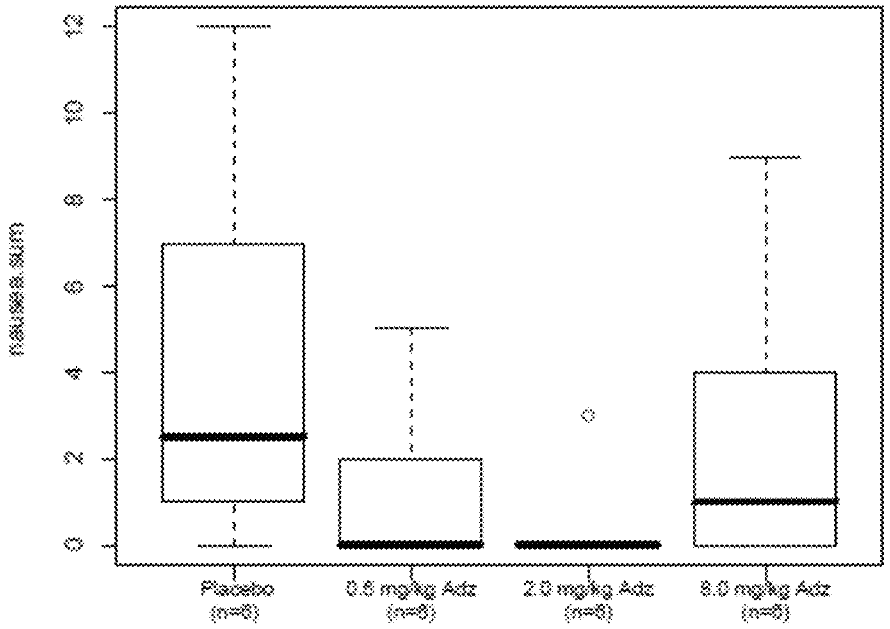
Figure 3:
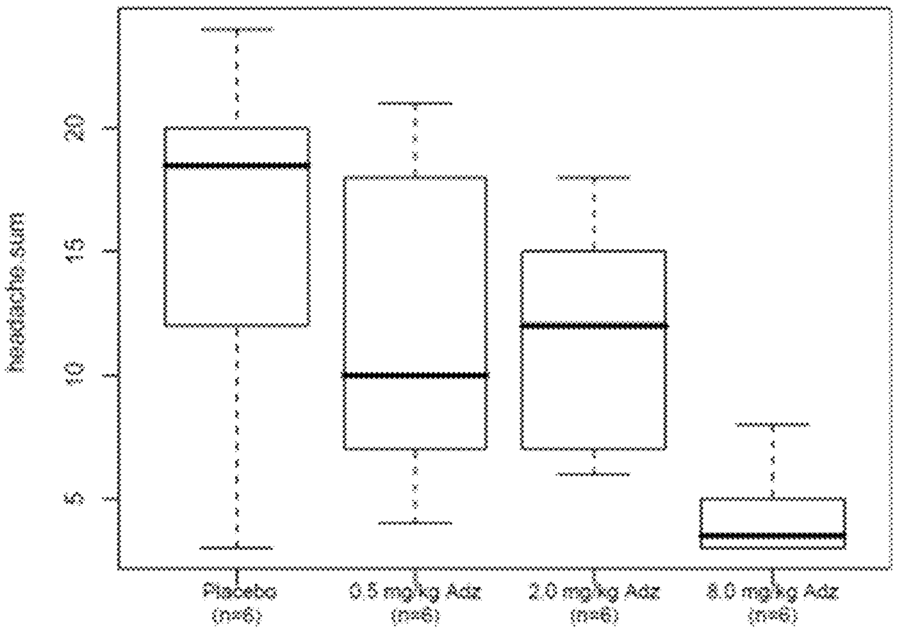
Figure 3:
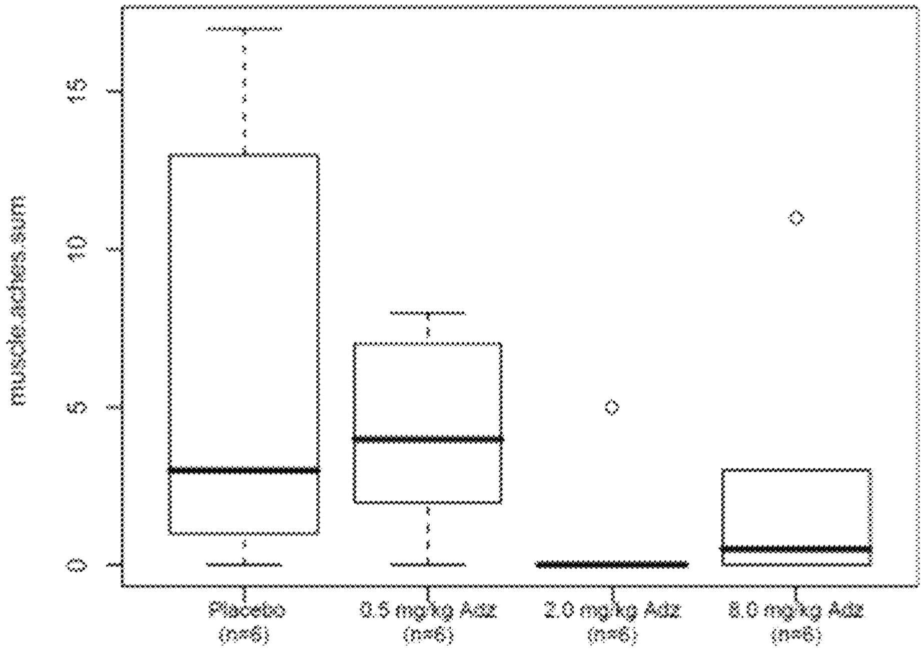
Figure 3:
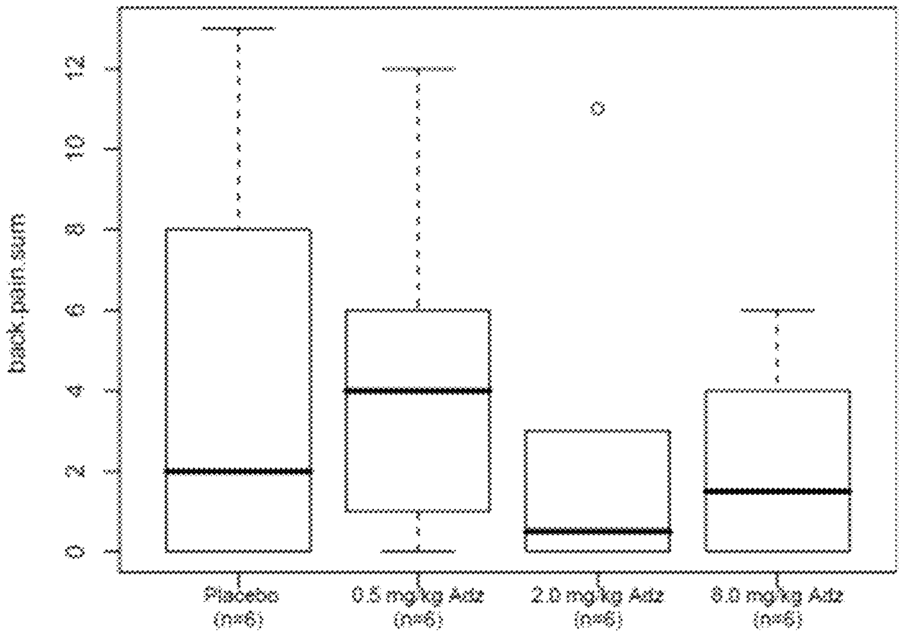
Figure 3:
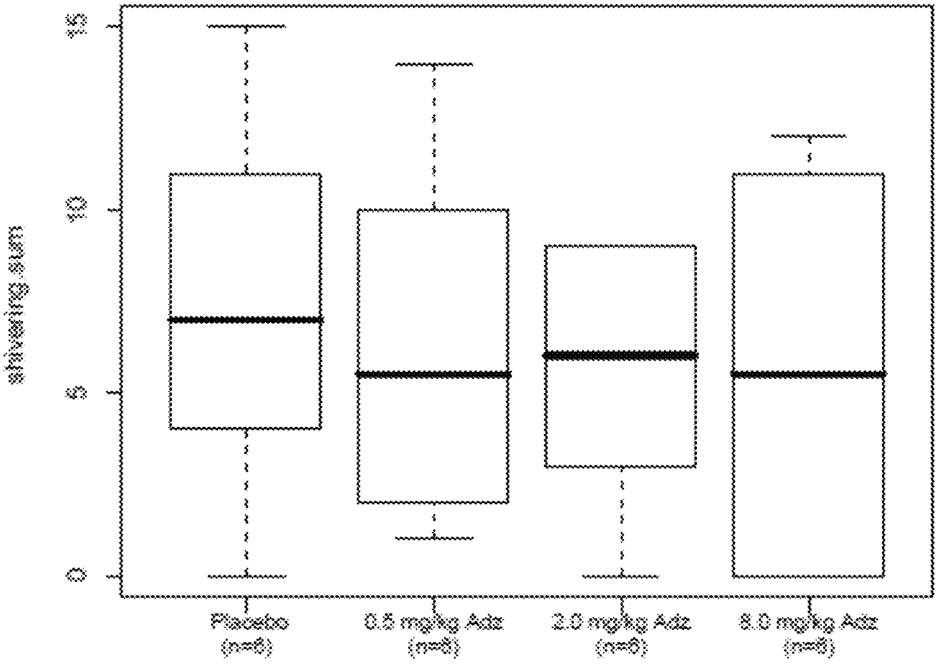
Figure 4:
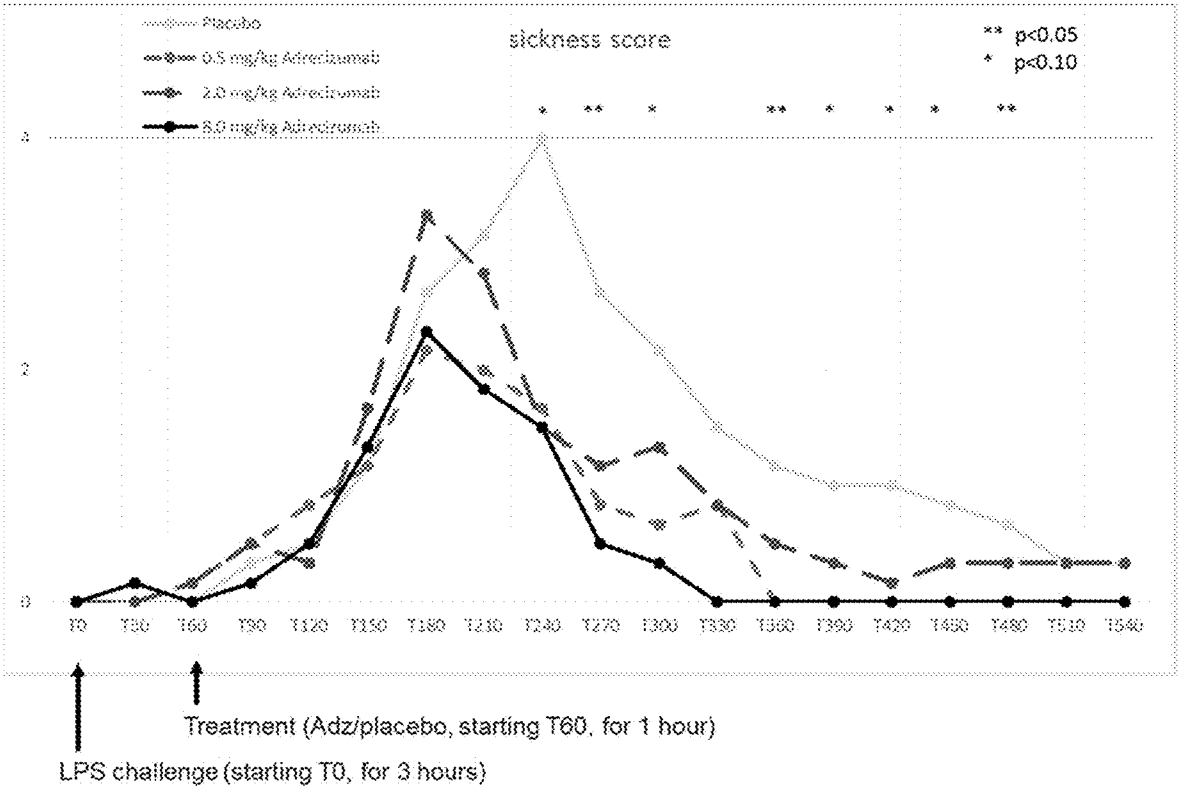
Figure 5:
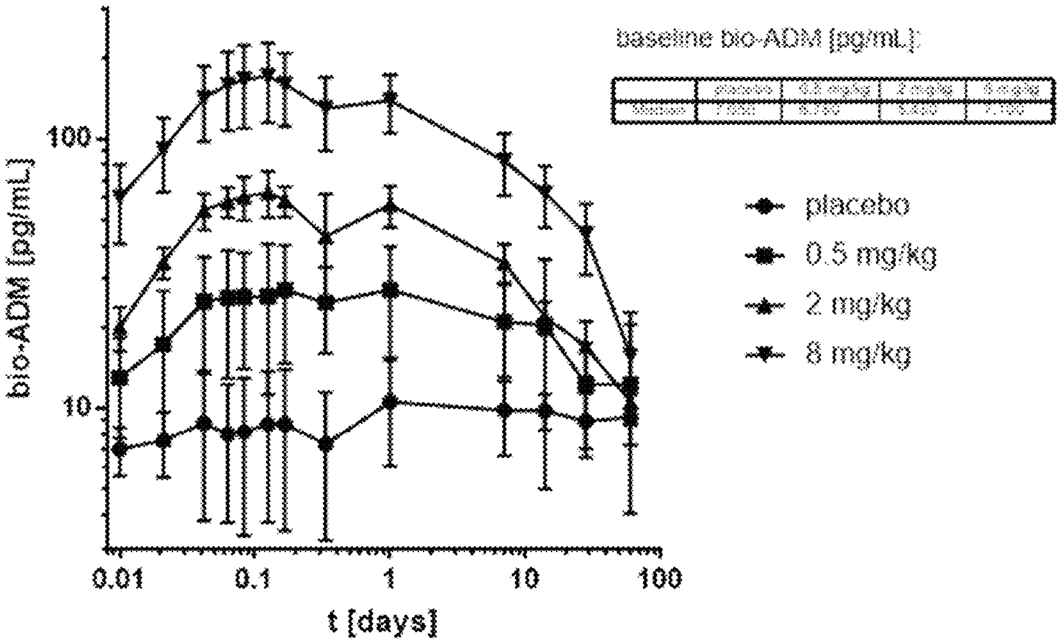

```
<160> NUMBER OF SEQ ID NOS: 24

<210> SEQ ID NO 1
<211> LENGTH: 52
<212> TYPE: PRT
<213> ORGANISM: Homo sapiens

<400> SEQUENCE: 1

Tyr Arg Gln Ser Met Asn Asn Phe Gln Gly Leu Arg Ser Phe Gly Cys
1               5                   10                  15

Arg Phe Gly Thr Cys Thr Val Gln Lys Leu Ala His Gln Ile Tyr Gln
            20                  25                  30

Phe Thr Asp Lys Asp Lys Asp Asn Val Ala Pro Arg Ser Lys Ile Ser
        35                  40                  45

Pro Gln Gly Tyr
    50


<210> SEQ ID NO 2
<211> LENGTH: 12
<212> TYPE: PRT
<213> ORGANISM: Homo sapiens

<400> SEQUENCE: 2

Cys Ala Pro Arg Ser Lys Ile Ser Pro Gln Gly Tyr
1               5                   10


<210> SEQ ID NO 3
<211> LENGTH: 22
<212> TYPE: PRT
<213> ORGANISM: Homo sapiens

<400> SEQUENCE: 3
```

```
Cys Thr Val Gln Lys Leu Ala His Gln Ile Tyr Gln Phe Thr Asp Lys
1               5                   10                  15

Asp Lys Asp Asn Val Ala
            20


<210> SEQ ID NO 4
<211> LENGTH: 21
<212> TYPE: PRT
<213> ORGANISM: Homo sapiens

<400> SEQUENCE: 4

Tyr Arg Gln Ser Met Asn Asn Phe Gln Gly Leu Arg Ser Phe Gly Cys
1               5                   10                  15

Arg Phe Gly Thr Cys
            20


<210> SEQ ID NO 5
<211> LENGTH: 8
<212> TYPE: PRT
<213> ORGANISM: Mus musculus

<400> SEQUENCE: 5

Gly Tyr Thr Phe Ser Arg Tyr Trp
1               5


<210> SEQ ID NO 6
<211> LENGTH: 8
<212> TYPE: PRT
<213> ORGANISM: Mus musculus

<400> SEQUENCE: 6

Ile Leu Pro Gly Ser Gly Ser Thr
1               5


<210> SEQ ID NO 7
<211> LENGTH: 11
<212> TYPE: PRT
<213> ORGANISM: Mus musculus

<400> SEQUENCE: 7

Thr Glu Gly Tyr Glu Tyr Asp Gly Phe Asp Tyr
1               5                   10


<210> SEQ ID NO 8
<211> LENGTH: 11
<212> TYPE: PRT
<213> ORGANISM: Mus musculus

<400> SEQUENCE: 8

Gln Ser Ile Val Tyr Ser Asn Gly Asn Thr Tyr
1               5                   10


<210> SEQ ID NO 9
<211> LENGTH: 9
<212> TYPE: PRT
<213> ORGANISM: Mus musculus

<400> SEQUENCE: 9

Phe Gln Gly Ser His Ile Pro Tyr Thr
1               5


<210> SEQ ID NO 10
<211> LENGTH: 225
<212> TYPE: PRT
```

<213> ORGANISM: Artificial Sequence
<220> FEATURE:
<223> OTHER INFORMATION: Description of Artificial Sequence: Synthetic
polypeptide

<400> SEQUENCE: 10

```
Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Arg Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Ser Thr Asn Tyr Asn Glu Lys Phe
    50                  55                  60

Lys Gly Lys Ala Thr Ile Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Thr Glu Gly Tyr Glu Tyr Asp Gly Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys His His His His His
    210                 215                 220

His
225
```

<210> SEQ ID NO 11
<211> LENGTH: 225
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 11

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Arg Tyr
            20                  25                  30

Trp Ile Ser Trp Val Arg Gln Ala Pro Gly Gln Gly Leu Glu Trp Met
        35                  40                  45

Gly Arg Ile Leu Pro Gly Ser Gly Ser Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
```

```
                85                  90                  95

Thr Glu Gly Tyr Glu Tyr Asp Gly Phe Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys His His His His His
    210                 215                 220

His
225


<210> SEQ ID NO 12
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Arg Tyr
            20                  25                  30

Trp Ile Glu Trp Val Arg Gln Ala Pro Gly Gln Gly Leu Glu Trp Met
        35                  40                  45

Gly Arg Ile Leu Pro Gly Ser Gly Ser Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Glu Gly Tyr Glu Tyr Asp Gly Phe Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205
```

```
Asn Thr Lys Val Asp Lys Arg Val Glu Pro Lys His His His His His
    210                 215                 220

His
225


<210> SEQ ID NO 13
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Gln Ser Gly Ala Glu Val Lys Lys Pro Gly Ser
1               5                   10                  15

Ser Val Lys Val Ser Cys Lys Ala Thr Gly Tyr Thr Phe Ser Arg Tyr
            20                  25                  30

Trp Ile Ser Trp Val Arg Gln Ala Pro Gly Gln Gly Leu Glu Trp Met
        35                  40                  45

Gly Glu Ile Leu Pro Gly Ser Gly Ser Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Glu Gly Tyr Glu Tyr Asp Gly Phe Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys His His His His His
    210                 215                 220

His
225


<210> SEQ ID NO 14
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Val Gln Ser Gly Ala Glu Val Lys Lys Pro Gly Ser
1               5                   10                  15

Ser Val Lys Val Ser Cys Lys Ala Thr Gly Tyr Thr Phe Ser Arg Tyr
            20                  25                  30
```

-continued

```
Trp Ile Glu Trp Val Arg Gln Ala Pro Gly Gln Gly Leu Glu Trp Met
        35                  40                  45

Gly Glu Ile Leu Pro Gly Ser Gly Ser Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Glu Gly Tyr Glu Tyr Asp Gly Phe Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys His His His His His
    210                 215                 220

His
225


<210> SEQ ID NO 15
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Asp Val Leu Leu Ser Gln Thr Pro Leu Ser Leu Pro Val Ser Leu Gly
1               5                   10                  15

Asp Gln Ala Thr Ile Ser Cys Arg Ser Ser Gln Ser Ile Val Tyr Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Ile Pro Tyr Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160
```

```
Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 16
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val Tyr Ser
            20                  25                  30

Asn Gly Asn Thr Tyr Leu Asn Trp Phe Gln Gln Arg Pro Gly Gln Ser
        35                  40                  45

Pro Arg Arg Leu Ile Tyr Arg Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Ile Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 17
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asp Val Val Met Thr Gln Ser Pro Leu Ser Leu Pro Val Thr Leu Gly
1               5                   10                  15
```

-continued

Gln Pro Ala Ser Ile Ser Cys Arg Ser Ser Gln Ser Ile Val Tyr Ser
20 25 30

Asn Gly Asn Thr Tyr Leu Glu Trp Phe Gln Gln Arg Pro Gly Gln Ser
35 40 45

Pro Arg Arg Leu Ile Tyr Arg Val Ser Asn Arg Asp Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Phe Gln Gly
85 90 95

Ser His Ile Pro Tyr Thr Phe Gly Gln Gly Thr Lys Leu Glu Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 18
<211> LENGTH: 19
<212> TYPE: PRT
<213> ORGANISM: Mus musculus

<400> SEQUENCE: 18

Tyr Arg Gln Ser Met Asn Gln Gly Ser Arg Ser Asn Gly Cys Arg Phe
1 5 10 15

Gly Thr Cys

<210> SEQ ID NO 19
<211> LENGTH: 12
<212> TYPE: PRT
<213> ORGANISM: Mus musculus

<400> SEQUENCE: 19

Cys Thr Phe Gln Lys Leu Ala His Gln Ile Tyr Gln
1 5 10

<210> SEQ ID NO 20
<211> LENGTH: 12
<212> TYPE: PRT
<213> ORGANISM: Mus musculus

<400> SEQUENCE: 20

Cys Ala Pro Arg Asn Lys Ile Ser Pro Gln Gly Tyr
1 5 10

<210> SEQ ID NO 21
<211> LENGTH: 12
<212> TYPE: PRT

<213> ORGANISM: Homo sapiens

<400> SEQUENCE: 21

Cys Thr Val Gln Lys Leu Ala His Gln Ile Tyr Gln
1 5 10

<210> SEQ ID NO 22
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Human antibody heavy chain with grafted mouse CDR

<400> SEQUENCE: 22

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Ser Arg Tyr
20 25 30

Trp Ile Glu Trp Val Arg Gln Ala Pro Gly Gln Gly Leu Glu Trp Ile
35 40 45

Gly Glu Ile Leu Pro Gly Ser Gly Ser Thr Asn Tyr Asn Gln Lys Phe
50 55 60

Gln Gly Arg Val Thr Ile Thr Ala Asp Thr Ser Thr Ser Thr Ala Tyr
65 70 75 80

Met Glu Leu Ser Ser Leu Arg Ser Glu Asp Thr Ala Val Tyr Tyr Cys
85 90 95

Thr Glu Gly Tyr Glu Tyr Asp Gly Phe Asp Tyr Trp Gly Gln Gly Thr
100 105 110

Thr Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val Glu Pro Lys Ser Cys Asp Lys Thr
210 215 220

His Thr Cys Pro Pro Cys Pro Ala Pro Glu Leu Leu Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr

```
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 23
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human antibody light chain with grafted mouse
      CDRs

<400> SEQUENCE: 23

Asp Val Val Leu Thr Gln Ser Pro Leu Ser Leu Pro Val Thr Leu Gly
1               5                   10                  15

Gln Pro Ala Ser Ile Ser Cys Arg Ser Ser Gln Ser Ile Val Tyr Ser
            20                  25                  30

Asn Gly Asn Thr Tyr Leu Glu Trp Tyr Leu Gln Arg Pro Gly Gln Ser
        35                  40                  45

Pro Arg Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Ile Pro Tyr Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175
```

-continued

```
Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 24
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Val Ser
1
```

The invention claimed is:

1. A pharmaceutical composition comprising an anti-adrenomedullin (ADM) antibody or an anti-adrenomedullin antibody fragment which binds to the N-terminal part (aa 1-21) of ADM: YRQSMNNFQGLRSFGCREGTC (SEQ ID No. 4) comprising the following sequence as a heavy chain:

SEQ ID NO: 22

QVQLVQSGAEVKKPGSSVKVSCKASGYTFSRYWIEWVRQAPGQGLEWIGE

ILPGSGSTNYNQKFQGRVTITADTSTSTAYMELSSLRSEDTAVYYCTEGY

EYDGFDYWGQGTTVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPGK and comprises the following sequence as a light chain:

SEQ ID NO: 23

DVVLTQSPLSLPVTLGQPASISCRSSQSIVYSNGNTYLEWYLQRPGQSPR

LLIYRVSNRFSGVPDRFSGSGSGTDFTLKISRVEAEDVGVYYCFQGSHIP

YTFGGGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC.

2. An antibody which binds to the N-terminal part (aa 1-21) of ADM: YRQSMNNFQGLRSFGCREGTC (SEQ ID No. 4) comprising the following sequences as a heavy chain:

SEQ ID NO: 22

QVQLVQSGAEVKKPGSSVKVSCKASGYTFSRYWIEWVRQAPGQGLEWIGE

ILPGSGSTNYNQKFQGRVTITADTSTSTAYMELSSLRSEDTAVYYCTEGY

-continued

EYDGFDYWGQGTTVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPGK or a sequence that is >95% identical to it and comprises the following sequence as a light chain:

SEQ ID NO: 23

DVVLTQSPLSLPVTLGQPASISCRSSQSIVYSNGNTYLEWYLQRPGQSPR

LLIYRVSNRFSGVPDRFSGSGSGTDFTLKISRVEAEDVGVYYCFQGSHIP

YTFGGGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC or a sequence that is >98% identical to it.

3. Pharmaceutical composition comprising a humanized monoclonal antibody according to claim 2.

4. An antibody comprising the following sequences as a heavy chain:

SEQ ID NO: 22

QVQLVQSGAEVKKPGSSVKVSCKASGYTFSRYWIEWVRQAPGQGLE

WIGEILPGSGSTNYNQKFQGRVTITADTSTSTAYMELSSLRSEDTAVYY

CTEGYEYDGFDYWGQGTTVTVSSASTKGPSVFPLAPSSKSTSGGTAAL

GCLVEDYFPEPVTVSWNSGALTSGVHTFPAVLQSSGLYSLSSVVTVPSS

SLGTQTYICNVNHKPSNTKVDKKVEPKSCDKTHTCPPCPAPELLGGPSV

FLFPPKPKDTLMISRTPEVTCVVVDVSHEDPEVKFNWYVDGVEVHNA

-continued

KTKPREEQYNSTYRVVSVLTVLHQDWLNGKEYKCKVSNKALPAPIEK

TISKAKGQPREPQVYTLPPSRDELTKNQVSLTCLVKGFYPSDIAVEWES

NGQPENNYKTTPPVLDSDGSFFLYSKLTVDKSRWQQGNVFSCSVMHE

ALHNHYTQKSLSLSPGK or a sequence that is >95% identical to it while also maintaining the sequences:

CDR1:

SEQ ID NO: 5

GYTFSRYW

CDR2:

SEQ ID NO: 6

ILPGSGST

CDR3:

SEQ ID NO: 7

TEGYEYDGFDY and comprises the following sequence as a light chain:

SEQ ID NO: 23

DVVLTQSPLSLPVTLGQPASISCRSSQSIVYSNGNTYLEWYLQRPGQSP

RLLIYRVSNRFSGVPDRFSGSGSGTDFTLKISRVEAEDVGVYYCFQGSIH

PYTFGGGTKLEIKRTVAAPSVFIFPPSDEQLKSGTASVVCLLNNFYPREA

KVQWKVDNALQSGNSQESVTEQDSKDSTYSLSSTLTLSKADYEKHKV

YACEVTHQGLSSPVTKSFNRGEC or a sequence that is >98% identical to it, while also maintaining the sequences:

CDR1:

SEQ ID NO: 8

QSIVYSNGNTY

CDR2:

RVS

CDR3:

SEQ ID NO: 9

FQGSHIPYT.

* * * * *